(12) United States Patent
Zan et al.

(10) Patent No.: US 12,253,489 B2
(45) Date of Patent: Mar. 18, 2025

(54) GAS SENSOR

(71) Applicant: NATIONAL CHIAO TUNG UNIVERSITY, Hsinchu (TW)

(72) Inventors: Hsiao-Wen Zan, Hsinchu (TW); Hsin-Fei Meng, Hsinchu (TW); Yu-Chi Lin, Hsinchu (TW); Shang-Yu Yu, Hsinchu (TW); Ting-Wei Tung, Taoyuan (TW); Yi-Chu Wu, Taichung (TW); Yu-Nung Mao, Tainan (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 89 days.

(21) Appl. No.: 17/975,977

(22) Filed: Oct. 28, 2022

(65) Prior Publication Data
US 2023/0049675 A1 Feb. 16, 2023

Related U.S. Application Data

(62) Division of application No. 16/515,206, filed on Jul. 18, 2019, now Pat. No. 11,499,937.

(30) Foreign Application Priority Data

Oct. 26, 2018 (TW) .................................. 107138044

(51) Int. Cl.
*G01N 27/407* (2006.01)
*G01N 27/12* (2006.01)
*G01N 33/00* (2006.01)

(52) U.S. Cl.
CPC ....... *G01N 27/4075* (2013.01); *G01N 27/125* (2013.01); *G01N 33/0027* (2013.01); *G01N 33/0075* (2013.01)

(58) Field of Classification Search
CPC ............. G01N 27/4075; G01N 27/125; G01N 33/0027; G01N 33/0075; G01N 27/128; G01N 27/126; G01N 27/127
See application file for complete search history.

(56) References Cited

U.S. PATENT DOCUMENTS

| 4,812,329 A | * | 3/1989 | Isenberg | ............ G01N 27/4075 |
| | | | | 427/126.6 |
| 2002/0011411 A1 | * | 1/2002 | Katafuchi | .......... G01N 27/4075 |
| | | | | 204/427 |

(Continued)

FOREIGN PATENT DOCUMENTS

| GB | 2519110 A | * | 4/2015 | ........... G01N 27/307 |
| JP | 2002214179 A | * | 7/2002 | |

(Continued)

OTHER PUBLICATIONS

Ming-Yen Chuang, et al. "Modulated gas sensor based on vertical organic diode with blended channel for ppb-regime detection", Sensors and Actuators B 230 (2016), pp. 223-230.

(Continued)

*Primary Examiner* — Kristina M Deherrera
*Assistant Examiner* — Fatemeh Esfandiari Nia

(57) ABSTRACT

A gas sensor includes a first electrode, a gas detecting layer disposed on the first electrode, and an electric-conduction enhanced electrode unit being electrically connected to the first electrode and the gas detecting layer. The electric-conduction enhanced electrode unit includes an electric-conduction enhancing layer and a second electrode electrically connected to the electric-conduction enhancing layer. The electric-conduction enhancing layer is electrically connected to the gas detecting layer and is made of an electrically conductive organic material.

13 Claims, 24 Drawing Sheets

(56) References Cited

U.S. PATENT DOCUMENTS

| | | | | |
|---|---|---|---|---|
| 2006/0249384 A1* | 11/2006 | Kim | ............... | G01N 27/127 |
| | | | | 204/424 |
| 2013/0233728 A1* | 9/2013 | Day | ............... | C04B 35/50 |
| | | | | 205/780.5 |
| 2014/0083851 A1* | 3/2014 | Chou | ............... | G01N 27/4075 |
| | | | | 204/431 |
| 2017/0067775 A1* | 3/2017 | Uhlin | ............... | G01V 1/18 |
| 2018/0266981 A1* | 9/2018 | Hansen | ............... | G01N 27/404 |
| 2019/0323985 A1* | 10/2019 | Xiao | ............... | G01N 33/0047 |
| 2020/0383844 A1* | 12/2020 | Suzuki | ............... | A61F 13/51113 |

FOREIGN PATENT DOCUMENTS

| | | | | |
|---|---|---|---|---|
| KR | 20170067775 A | * | 6/2017 | ......... G01N 27/4075 |
| TW | 201224446 A | * | 6/2012 | ........... G01N 27/127 |
| TW | 201612099 A | | 4/2016 | |

OTHER PUBLICATIONS

F. Razi, et al. "Investigation of hydrogen sensing properties and aging effects of Schottky like Pd/porous Si", Sensors and Actuators B 146 (2010), pp. 53-60.

* cited by examiner

GAS SENSOR

CROSS-REFERENCE TO RELATED APPLICATION

This application is a divisional application of United States Non-Provisional Ser. No. 16/515,206, filed on Jul. 18, 2019, now U.S. Pat. No. 11,499,937 B2, to which priority is claimed under 35 U.S.C. § 120 and further claims priority under 35 U.S.C. § 119 to Taiwanese Invention Patent application No. 107138044, filed on Oct. 26, 2018. The entire disclosure of United States Non-Provisional patent application Ser. No. 16/515,206 and Taiwanese Invention Patent application No. 107138044 are hereby expressly incorporated by reference.

FIELD

The disclosure relates to a gas sensor, more particularly to a gas sensor including an electric-conduction enhanced electrode unit.

BACKGROUND

In recent years, due to increasingly serious air pollution problems, gas sensors are becoming more important. A conventional gas sensor with nanostructures has excellent gas sensing properties, and thus has a wide range of applications, from being used in daily life, such as in carbon monoxide detectors or smoke detectors, to being applied to the detection of explosive or harmful gases in factories. The operation of the conventional gas sensor is mostly performed through measurement of the change of the resistance value after its component material reacts with the gas to be detected.

Even though the conventional gas sensor with multi-layer side walls can accurately detect the gas to be detected by changing the sensing layer material, its sensitivity still needs to be improved as to enhance the efficiency of the gas sensor.

In order to increase the surface area for reaction between the sensing material and the gas to be detected so as to improve the sensing efficiency of the gas sensor, the inventors have previously used electrode formed with nanometer micropores which the gas penetrates to reaction with the sensing material. The increased surface area for reaction improved the efficiency of the gas sensor.

In order to produce these electrodes formed with a plurality of micropores, first, several nano-spheres are attached to a semi-finished product, then, a metal layer is formed on the semi-finished product in a plating manner, and finally, the nano-spheres are removed so as to get the final finished product. However, it is not easy to control the stable distribution and attachment of the nanospheres, and uneven distribution of the nanospheres affects the number and distribution of the micropores on the subsequently formed electrodes, which may, in turn, affect the sensing results. Thus, mass production of the conventional gas sensors with the microspore is difficult. In addition, the steps of coating and removal of nanospheres significantly lengthens the manufacturing process, making the conventional gas sensor even less suitable for mass production.

SUMMARY

Therefore, the object of the disclosure is to provide a gas sensor that can alleviate at least one of the drawbacks of the prior art.

According to a first aspect of the disclosure, a gas sensor includes a first electrode, a gas detecting layer disposed on the first electrode, an electric-conduction enhanced electrode unit being electrically connected to the first electrode and the gas detecting layer, and an insulating unit. The electric-conduction enhanced electrode unit includes an electric-conduction enhancing layer and a second electrode electrically connected to the electric-conduction enhancing layer. The electric-conduction enhancing layer is electrically connected to the gas detecting layer and is made of an electrically conductive organic material. The insulating unit is disposed on the first electrode for partially separating the first electrode from the gas detecting layer and the electric-conduction enhanced electrode unit.

According to a second aspect of the disclosure, a gas sensor includes a first electrode, a gas detecting layer disposed on the first electrode, an electric-conduction enhancing electrode unit electrically connected to the first electrode and the gas detecting layer.

The electric-conduction enhanced electrode unit includes an electric-conduction enhancing layer and a second electrode electrically connected to the electric-conduction enhancing layer. The electric-conduction enhancing layer is electrically connected to the gas detecting layer and is made of an electrically conductive organic material The second electrode of the electric-conduction enhanced electrode unit includes a plurality of spaced-apart electrode portions formed on the gas detecting layer and interposed between the electric-conduction enhancing layer and the gas detecting layer. Any two adjacent ones of the electrode portions are formed with a second gap therebetween to expose the gas detecting layer from the second gap. The electric-conduction enhancing layer extends into the second gaps to be in contact with the gas detecting layer.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
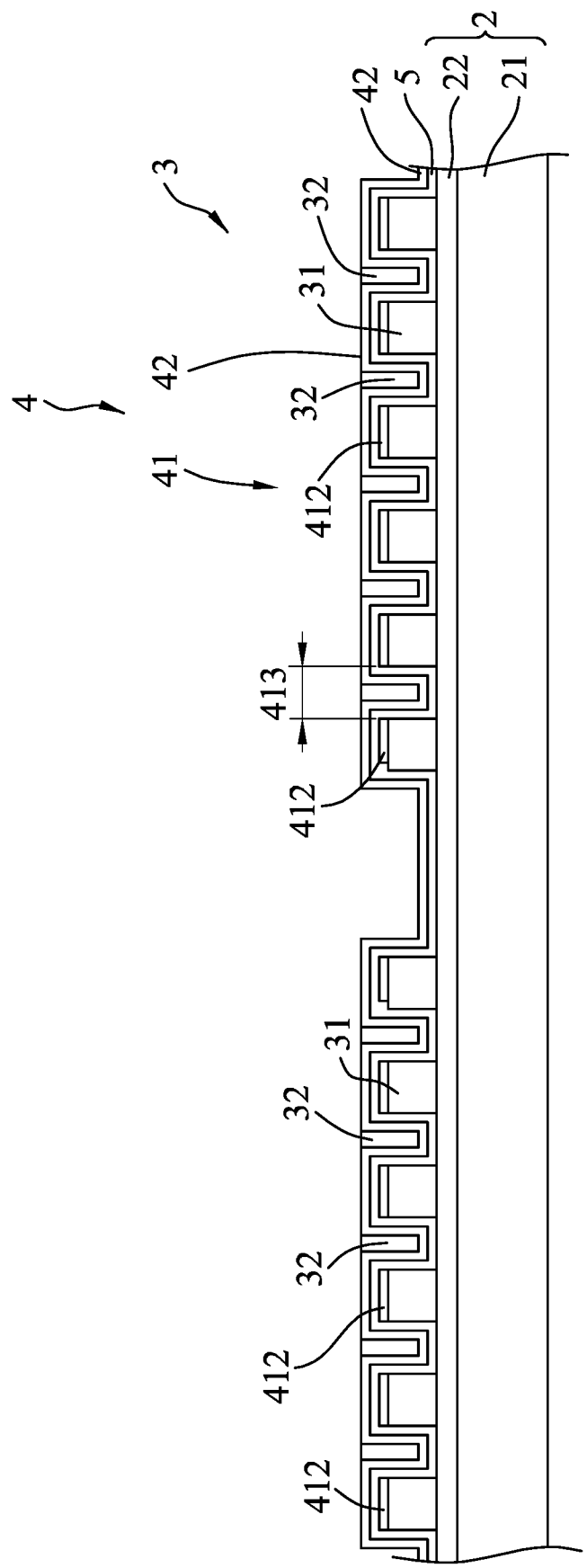
FIG. 1 is a schematic sectional view of a first embodiment of a gas sensor according to the disclosure.

Before the present invention is described in greater detail, it should be noted that where considered appropriate, reference numerals or terminal portions of reference numerals have been repeated among the figures to indicate corresponding or analogous elements, which may optionally have similar characteristics.

Figure 2:
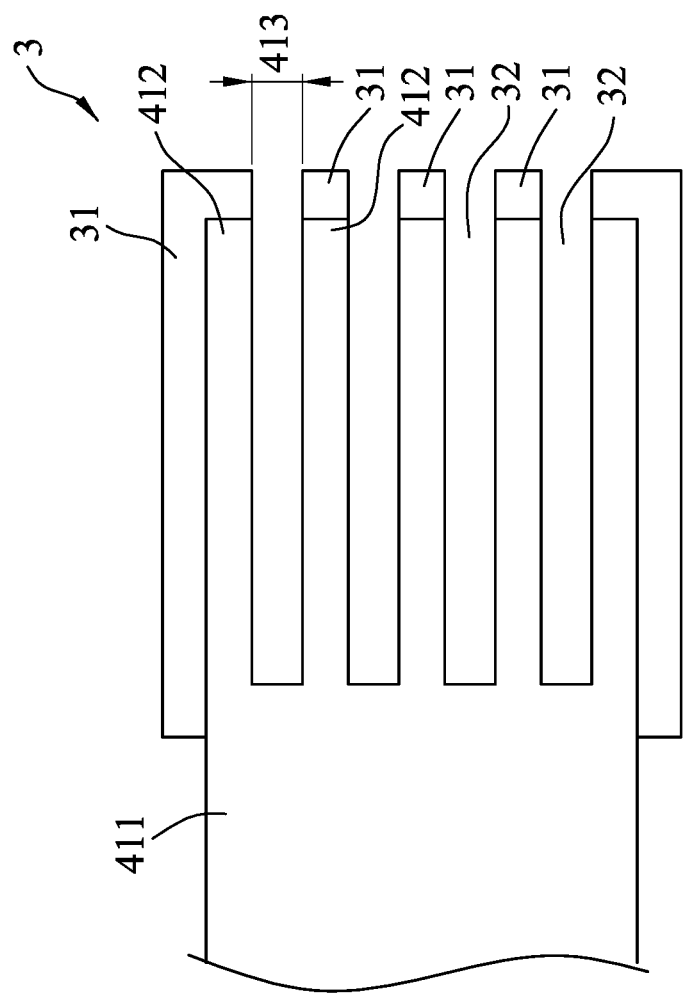
FIG. 2 is a fragmentarily schematic top view illustrating a second electrode and an insulating unit of the first embodiment.

Referring to FIGS. 1 and 2, a first embodiment of a gas sensor according to the disclosure includes a substrate 2, a gas detecting layer 5, an electric-conduction enhanced electrode unit 4, and an insulating unit 3. The substrate 2 includes a substrate body 21 and a first electrode 22 formed on the substrate body 21. The substrate body 21 serves as a supporting substrate and maybe made of an electrically insulating material selected from polymers, glass, or ceramic. The first electrode 22 may be made of an electrically conductive material selected from metal, electrically conductive metallic compound or electrically conductive organic material, for example, gold, aluminum, silver, calcium, zinc oxide, indium tin oxide, molybdenum oxide, lithium fluoride, etc. In this embodiment, the material of the first electrode 22 is exemplified as indium tin oxide (ITO).

The gas detecting layer 5 is disposed on the first electrode 22 oppositely of the substrate body 21. The electric-conduction enhanced electrode unit 4 is electrically connected to the first electrode 22 and the gas detecting layer 5 and includes an electric-conduction enhancing layer 42 and a second electrode 41 electrically connected to the electric-conduction enhancing layer 42. The electric-conduction enhancing layer 42 is electrically connected to the gas detecting layer 5 and is made of an electrically conductive organic material.

In alternative embodiments where the first electrode 22 has supporting properties, the substrate body 21 may be omitted from the substrate 2.

Figure 4:
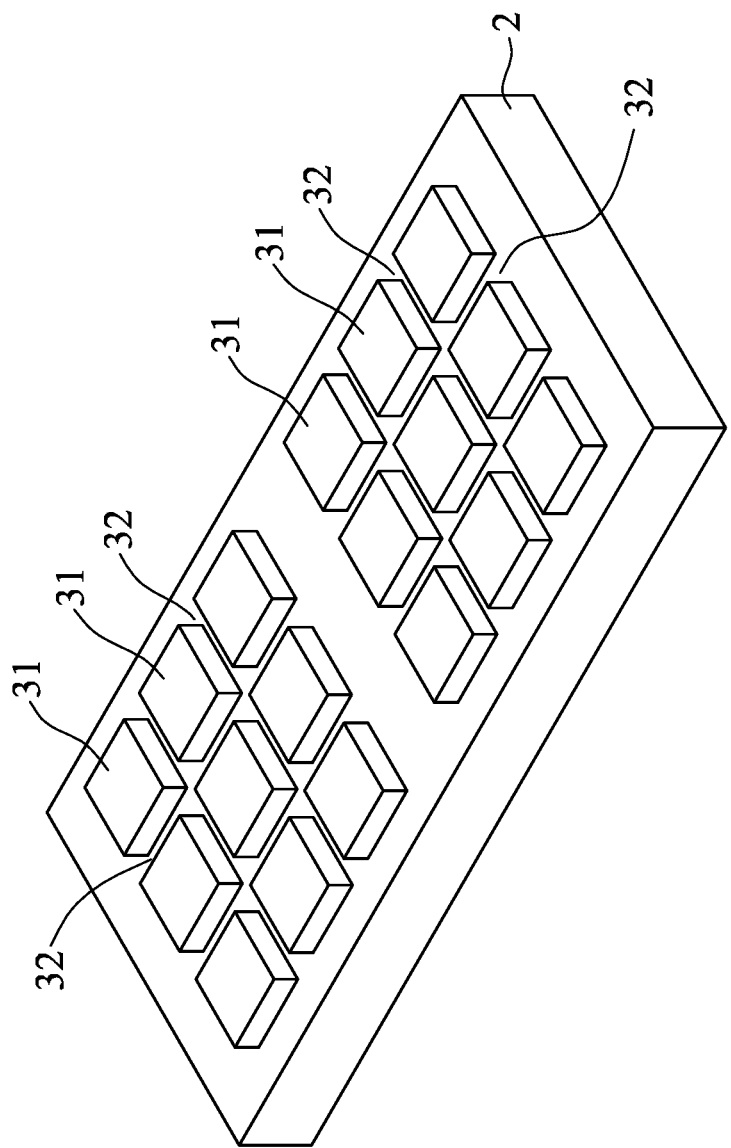
FIG. 4 is a perspective view, illustrating another configuration of the insulating unit of the first embodiment.

The insulating unit 3 is disposed on the first electrode 22 for partially separating the first electrode 22 from the gas detecting layer 5 and the electric-conduction enhanced electrode unit 4. The insulating unit 3 includes a plurality of insulating members 31 disposed on the first electrode 22. Any two adjacent ones of the insulating members 31 are formed with a first gap 32 therebetween so as to expose the first electrode 22 from the first gap 32, each of the first gaps 32 being surrounded by two corresponding adjacent ones of the insulating members 31. In a variation of the first embodiment, the first gaps 32 are in spatial communication with each other (see FIG. 4) to separate the insulating members 31 from each other. The insulating members 31 maybe made of an electrically insulating material selected from poly(4-vinylphenol) (abbreviated as PVP) or polymethylmethacrylate (abbreviated as PMMA).

The gas detecting layer 5 disposed on the first electrode 22 is reactive with a gas to be detected. Upon reaction with the gas to be detected, one or more electrical properties of the gas detecting layer 5 may change. These changes in the electrical properties may be measured using the first and second electrodes 22, 41 electrically connected to the gas detecting layer 5 so as to determine the presence of the gas to be detected. In this embodiment, as an example, a change in the electrical current flowing through the gas detecting layer 5, which is caused by a change in electrical resistance of the gas detecting layer 5 upon reaction with the gas to be detected, is measured.

The gas detecting layer 5 may be made of an organic material, an inorganic material, or a composite material of organic and inorganic materials. For example, the material for making the gas detecting layer 5 may be selected from, but is not limited to, the organic material including benzene dithieno-thiophene[3,4-b] thiophene copolymer such as poly[[4,8-bis[(2-ethylhexyl)oxy]benzo[1,2-b:4,5-b'] dithiophene-2,6-diyl][3-fluoro-2-[(2-ethylhexyl)car bonyl]thieno [3,4-b]thiophenediyl]](abbreviated as PTB7), 9,9-dioctylfluorene-N-(4-butylphenyl) diphenylamine copolymer such as poly[(9,9-dioctylfluorenyl-2,7-diyl)-alt-(4,4'-(N-(4-butylphenyl)-diphenylamine] (abbreviated as TFB), poly(9,9-dioctylfluorene) (abbreviated as PFO), poly (9,9-dioctylfluorene-alt-benzothiadiazole) (abbreviated as F8BT), poly[4,8-bis(5-(2-ethylhexyl) thiophene-2-yl)-benzo [1,2-b;4,5-b']dithiophene-2,6-diyl-alt-(4-(2-ethylhexyloxy-carbonyl)-3-fluoro-thie no[3,4-b]thiophene-)-2,6-diyl] (abbreviated as PBDTTT-EFT), poly[4,8-bis(5-(2-ethylhexyl) thiophene-2-yl)-benzo[1,2-b;4,5-b']dithiophene-2,6-diyl-alt-(4-(2-ethylhexanoyl)-thieno[3,4-b]-thiophene-)-2,6-diyl] (abbreviated as PBDTTT-CT], and poly(3-hexylthiophene- 2,5-diyl) (abbreviated as P3HT), or the inorganic material including carbon, silicon, zinc oxide (ZnO), tungsten oxide ($WO_3$), titanium dioxide ($TiO_2$) and indium gallium oxide (IGZO).

The second electrode 41 includes a connecting portion 411 and a plurality of spaced-apart electrode portions 412 extending from the connecting portion 411. The second electrode 41 may be made of an electrically conductive material selected from a metal such as aluminum, gold, silver, nickel, etc, a metallic compound such as indium tin oxide, zinc oxide, molybdenum oxide, lithium fluoride, etc, or an organic material such as poly (3,4-ethylenedioxythiophene)-poly(styrene sulfonate) (PEDOT: PSS). In one form, the second electrode 41 may be single-layered or multi-layered. Since the electrically conductive material that may be used for making the second electrode 41 is well known in the art, further details are omitted for the sake of brevity. In this embodiment, the material of the second electrode 42 is exemplified as aluminum.

In this embodiment, the electric-conduction enhancing layer 42 and the gas detecting layer 5 extend into the first gaps 32 so as to be electrically connected with the first electrode 22 and incompletely fill the first gaps 32, thereby increasing a gas-sensing area of the gas sensor. The electrically conductive organic material for making the electric-conduction enhancing layer 42 may be selected from the group consisting of poly (3,4-ethylenedioxythiophene) (abbreviated as PEDOT), polystyrene sulfonate, polypyrrole (abbreviated as PPY), polythiophene (abbreviated as PT), polyphenylene sulfide (abbreviated as PPS), polyaniline (abbreviated as PANI), polyacetylene (abbreviated as PAC), or poly(p-phenylene vinylene) (abbreviated as PPV), and combinations thereof.

In this embodiment, the gas detecting layer 5 covers the insulating members 31 and extends into the first gaps 32 to cover the first electrode 22 exposed therefrom, and the electric-conduction enhancing layer 42 covers the gas detecting layer 5. Any two adjacent ones of the spaced-apart electrode portions 412 are formed with a second gap 413 therebetween. Each of the spaced-apart electrode portions 412 is disposed between a corresponding one of the insulating members 31 and the gas detecting layer 5. Each of the second gaps 413 is in spatial communication with a corresponding one of the first gaps 32 such that the gas detecting layer 5 and the electric-conduction enhancing layer 42 extend into the corresponding first gap 32 through the second gap 413.

The purpose of arranging the electrode portions 412 is to cooperate with the electric-conduction enhancing layer 42 to conduct a detecting current along with the gas detecting layer 5, and the electrode portions 412 may have a number of configurations in actual practice.

Figure 3:
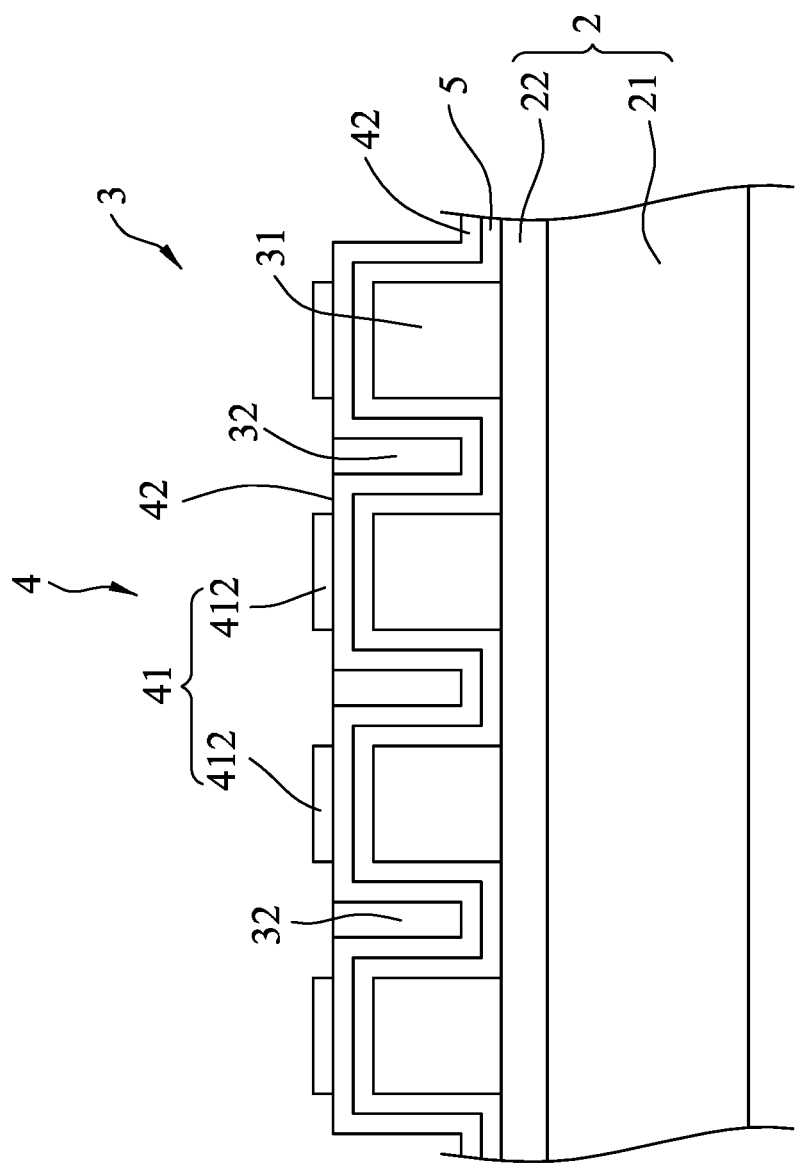
FIG. 3 is a fragmentarily schematic sectional view of a variation of the first embodiment.

In a variation of this embodiment, as shown in FIG. 3, each of the electrode portions 412 are instead disposed on the electric-conduction enhancing layer 42 and oppositely corresponding in position to a corresponding one of the insulating members 31.

Figure 5:
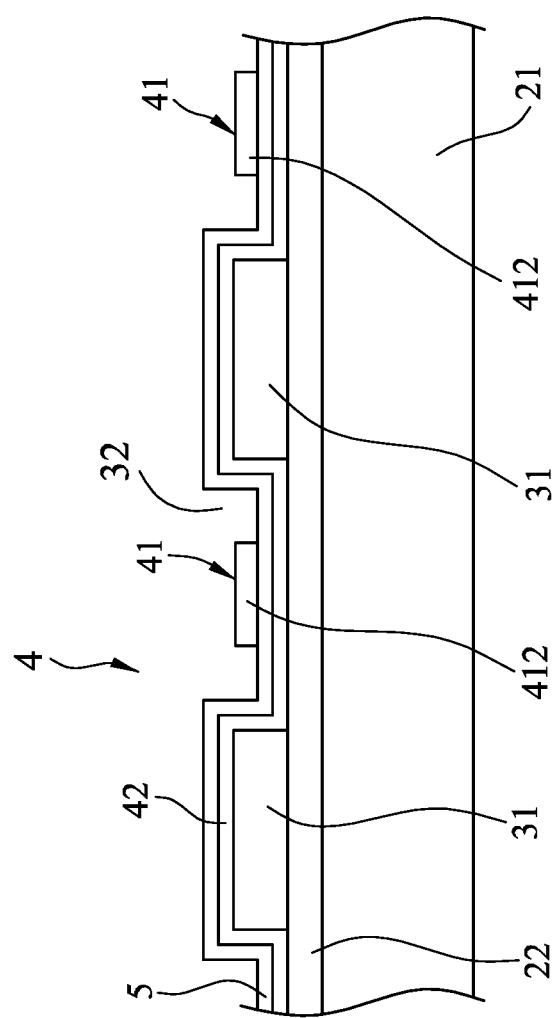
FIG. 5 is a fragmentarily schematic sectional view of another variation of the first embodiment.

Referring to FIG. 5, in yet another variation of this embodiment, the electric-conduction enhancing layer 42 covers the insulating members 31 and extends into the first gaps 32 to cover the first electrode 22 exposed therefrom, and the gas detecting layer 5 covers the electric-conduction enhancing layer 42. Each of the electrode portions 412 is disposed on the gas detecting layer 5 oppositely of the first electrode 22 and in a corresponding one of the first gaps 32.

Referring back to FIG. 2, in this embodiment of the disclosure, the electric-conduction enhancing layer 42 made of the electrically conductive organic material is arranged in cooperation with formation of the second electrode 41 into a grating structure. When a voltage is applied to the gas sensor, the electric-conduction enhancing layer 42 may act as an electrode cooperatively with the second electrode 41. This increases the surface area of the gas detecting layer 5 that current may flow through, which improves sensitivity of the gas sensor.

Furthermore, since the spaced-apart electrode portions 412 may be formed by film-coating and lithography, the production cost is lowered and precision of the width of the second gaps 413 among the electrode portions 412 is improved. Additionally, the simplified production is also suitable for mass production.

In the following, a preparation example of the first embodiment of the gas sensor is provided. First, the first electrode 22 and the insulating unit 3 are sequentially formed on the substrate body 21. Then, the spaced-apart electrode portions 412 are respectively formed on the insulating members 31 using film-coating and lithography. Finally, the gas detecting layer 5 and the electric-conduction enhancing layer 42 are coated onto the insulating members 31 respectively formed with the electrode portions 412, extend into the first gaps 32 among the insulating members 31 through the corresponding second gaps 413, and are coated onto the first electrode 22 exposed from said first gaps 32 to obtain the gas sensor as shown in FIG. 1.

Since the spaced-apart electrode portions 412 can be formed using film-coating and lithography, the width of the second gaps 413 thereamong may be varied depending on designs or sizes of the gas sensor as needed. For example, the width of the second gaps 413 may be between 1 micrometer and 1 centimeter. In some embodiments, the width may be smaller than 300 micrometers to keep the electrode portions 412 relatively proximal to each other, thereby producing better coupling effect between the electric-conduction enhancing layer 42 and the electrode portions 412. Consequently, a higher detecting current is detectable even when a smaller voltage is applied to the gas sensor. In certain embodiments, the width is between 1 micrometer and 200 micrometers. In certain embodiments, the width is between 5 micrometers and 80 micrometers. In certain embodiments, the width is between 10 micrometers and 80 micrometers. In certain embodiments, the width is between 5 micrometers and 30 micrometers. In certain embodiments, the width is between 10 micrometers and 30 micrometers.

In certain embodiments, the insulating unit 3 may include only one of the insulating members 31 in the absence of any first gaps 32, with the gas detecting layer 5 directly covering the insulating member 31 and extending to the surface of the first electrode 22.

Figure 6:
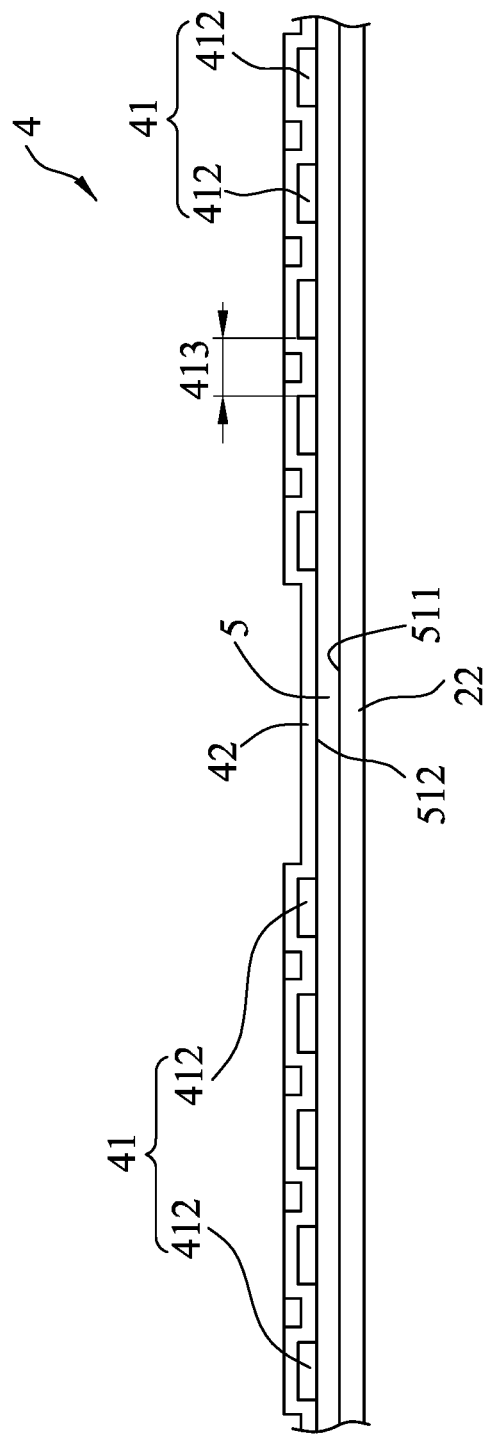
FIG. 6 is a fragmentarily schematic sectional view of a second embodiment of a gas sensor according to the disclosure.

Referring to FIG. 6, a second embodiment of the gas sensor according to the disclosure is illustrated. In this embodiment, the gas sensor is similar to the gas sensor the first embodiment in including the gas detecting layer 5, the first and second electrode 22, 41, and the electric-conduction enhancing layer 42. The first and second electrode 22, 41 and the electric-conduction enhancing layer 42 are the same as the first embodiment and details of the structures and materials thereof are omitted for the sake of brevity. Specifically, in the second embodiment, the gas detecting layer 5 has opposite first and second surfaces 511, 512. The first electrode 22 is disposed on the first surface 511 of the gas detecting layer 5. The spaced-apart electrode portions 412 are formed on the second surface 512 of the gas detecting layer 5 and interposed between the electric-conduction enhancing layer 42 and the gas detecting layer 5. The gas detecting layer 5 is exposed from the second gaps 413 and the electric-conduction enhancing layer 42 extends into the second gaps 413 to be in contact with the gas detecting layer 5.

In one form, the gas detecting layer 5 may be composed of an absorbent base material with supporting properties and a gas detecting material absorbed onto the absorbent base material.

In certain embodiments, the absorbent base material is porous.

A preparation example of the second embodiment is provided. First, the gas detecting material is absorbed onto the absorbent base material to form the gas detecting layer 5. Then, respective formation of the first electrode 22 on the first surface 511 of the gas detecting layer 5 and formation of the spaced-apart electrode portions 412 on the second surface 512 of the gas detecting layer 5 are carried out using film-coating and lithography. Finally, the electric-conduction enhancing layer 42 is covered over the spaced-apart electrode portions 412 and the portions of the gas detecting layer 5 exposed from the second gaps 413 among the electrode portions 412. Examples of the absorbent base material may include oil blotting paper, tissue paper, etc, but is not limited thereto, as long as the material has the supporting properties and is available for the gas detecting material to be absorbed thereon. In this embodiment, the absorbent base material is exemplified as oil blotting paper.

Since the gas detecting layer 5 has both supporting properties and is reactive with the gas to be detected, the first and the second electrodes 22, 41 maybe formed directed onto the gas detecting layer 5, which further simplifies the production of the gas sensor of the disclosure.

Figure 7:
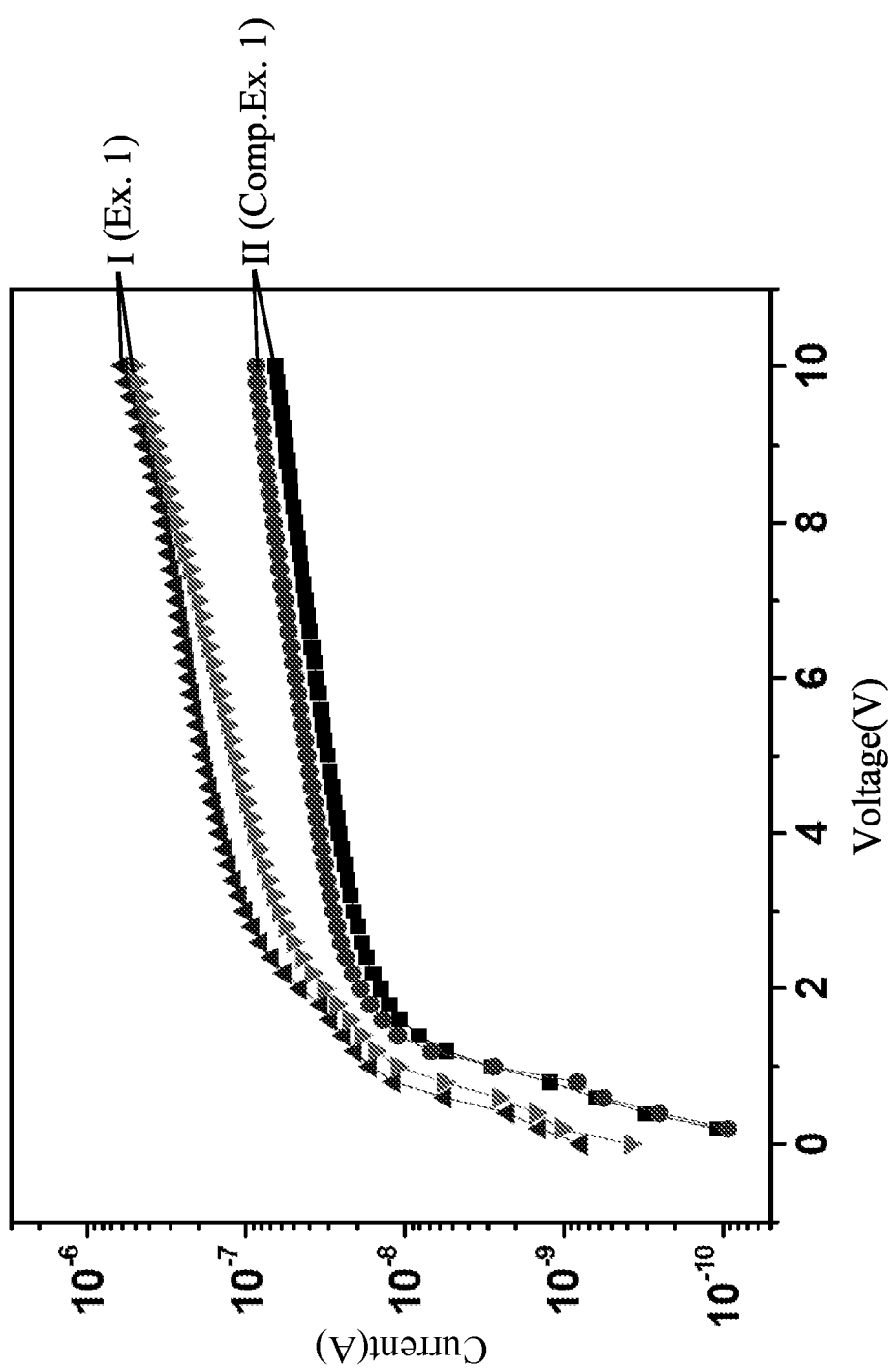
FIG. 7 is a graph of current versus voltage illustrating comparison of a detecting current-applied voltage relationship of Example 1 of the first embodiment with that of Comparative Example 1.

Referring to FIG. 7, comparison of the detecting current-applied voltage relationship of the gas sensor of Example 1 of the first embodiment with that of Comparative example 1 is illustrated. The curves of Groups (I) and (II) respectively represent results of duplicate experiments in which the detecting current is measured at an applied voltage range of 0 volt to 10 volts using Example 1 and Comparative example 1. The gas sensor of Example 1 has the electric-conduction enhancing layer 42 made of PEDOT, the gas detecting layer 5 made of PTB7, and the second gaps 413 of the second electrode 41 with a width of 10 micrometers (μm). The gas sensor of Comparative example 1 has a structure and a constituting composition similar to that of the Example 1 except for the omission of the electric-conduction enhancing layer 42.

Figure 8:
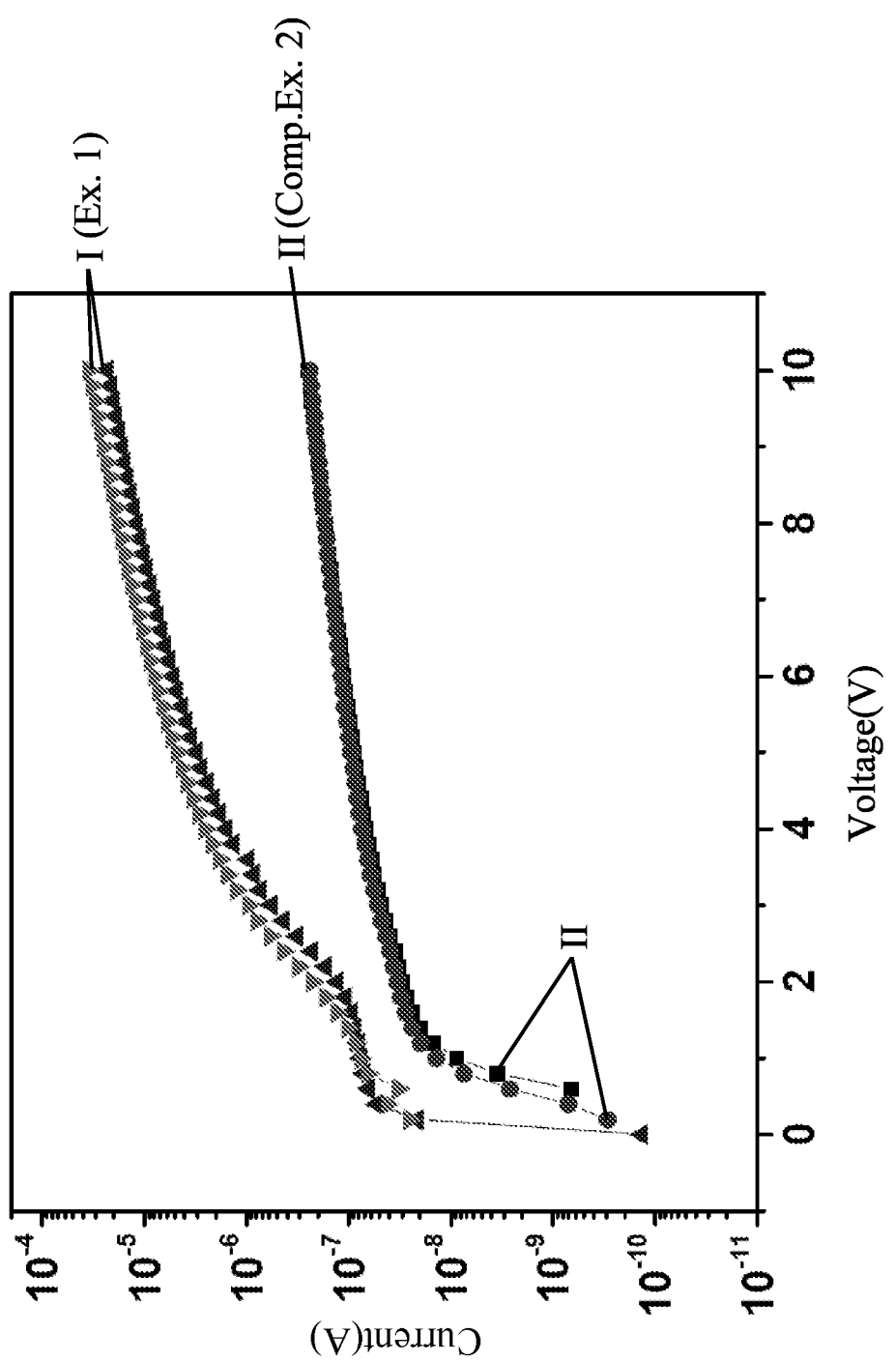
FIG. 8 is a graph of current versus voltage illustrating comparison of a detecting current-applied voltage relationship of Example 2 of the first embodiment with that of Comparative Example 2.
Figure 9:
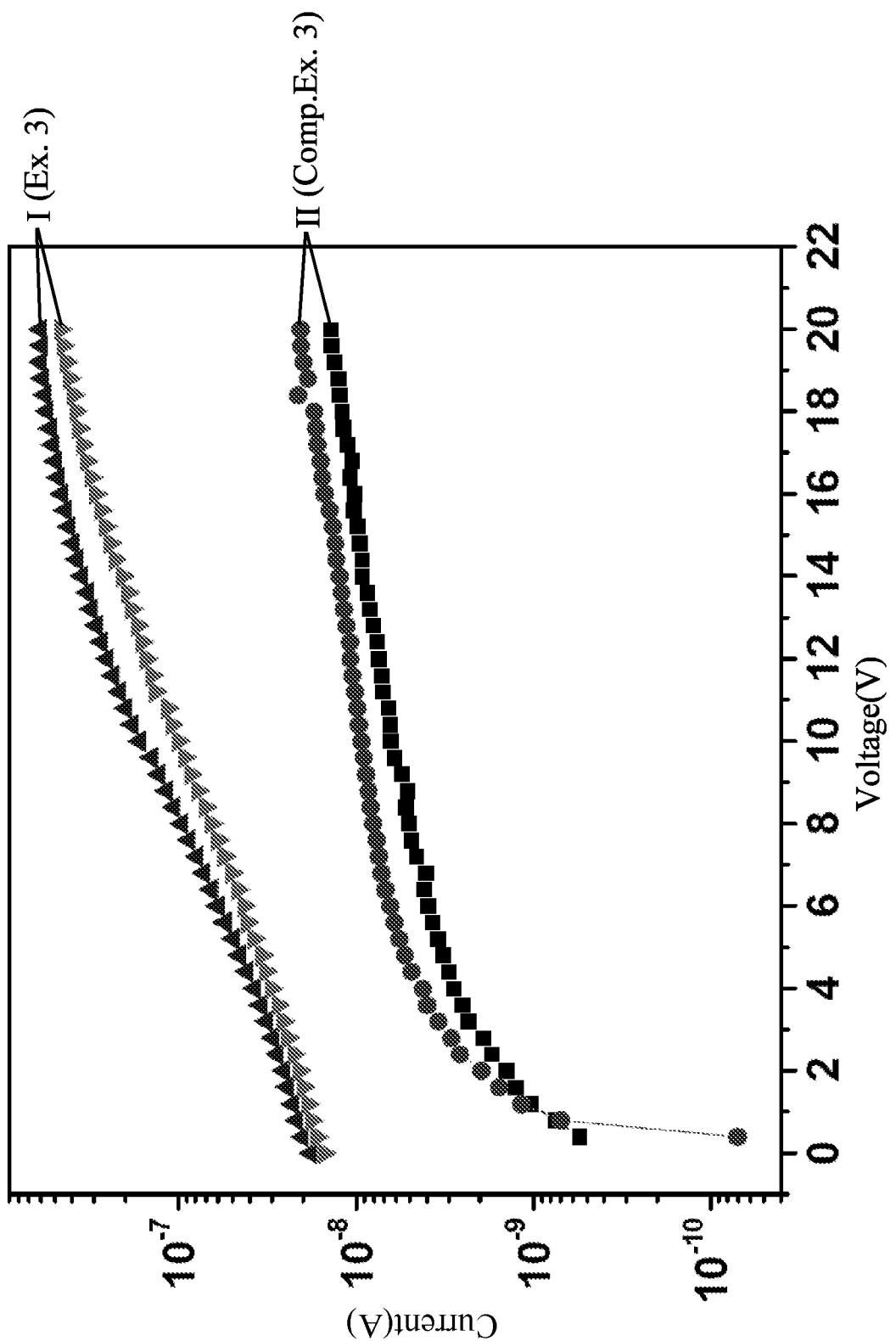
FIG. 9 is a graph of current versus voltage illustrating comparison of a detecting current-applied voltage relationship of Example 3 of the first embodiment with that of Comparative Example 3.

FIGS. 8 to 9 respectively illustrate comparison of the detecting current-applied voltage relationship of the gas sensor of Examples 2 and 3 of the first embodiment with that of Comparative examples 2 and 3, in a manner similar to FIG. 7. The gas sensors of Examples 2 and 3 have a structure and a constituting composition similar to that of Example 1, but the widths of the second gaps 413 of the second electrodes 41 thereof are 20 μm and 80 μm, respectively. Comparative examples 2 and 3 have structures and constituting compositions respectively similar to that of Examples 2 and 3, but both lack the electric-conduction enhancing layer 42.

Figure 10:
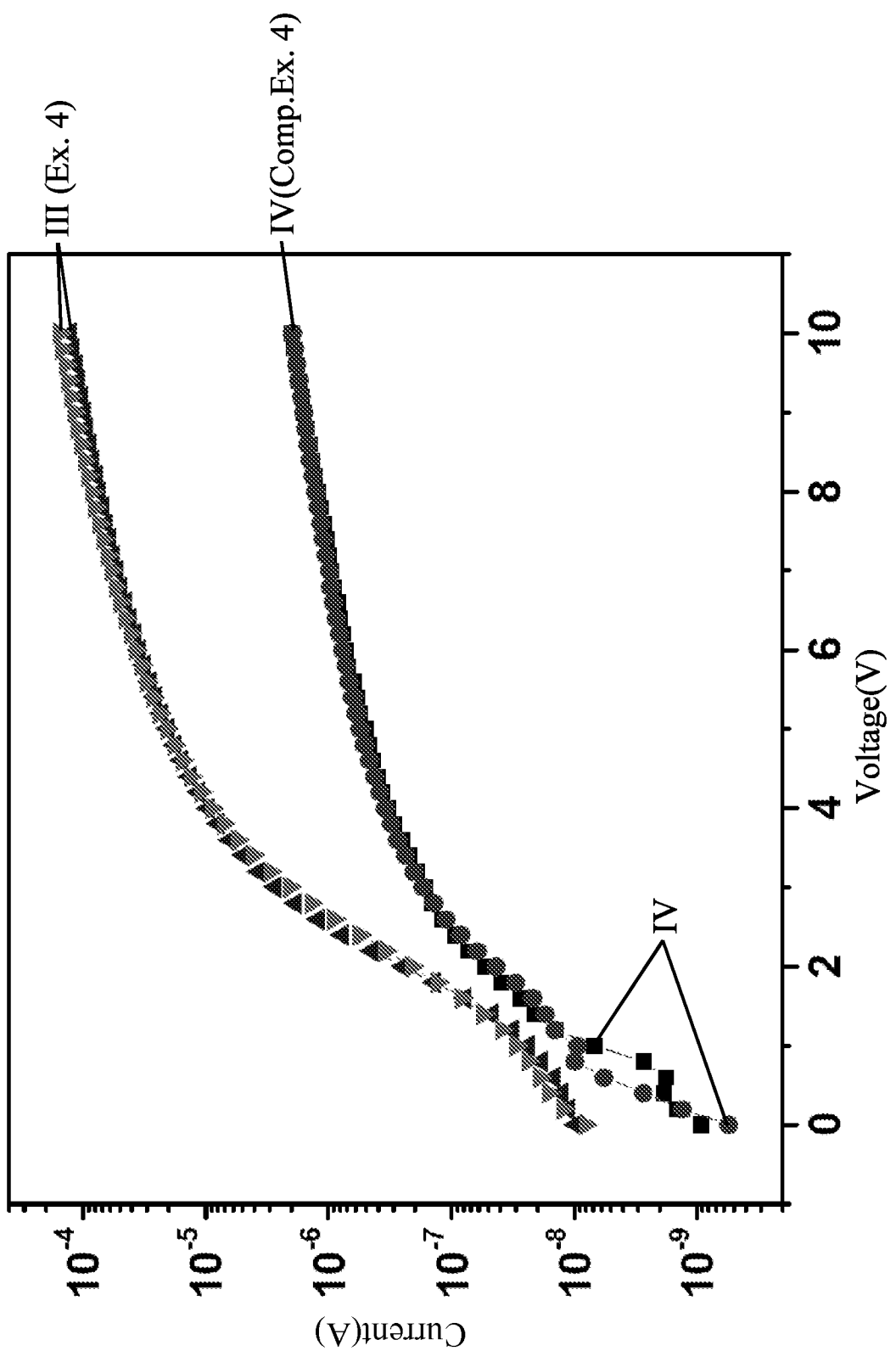
FIG. 10 is a graph of current versus voltage illustrating comparison of a detecting current-applied voltage relationship of Example 4 of the first embodiment with that of Comparative Example 4.

Referring to FIG. 10, comparison of the detecting current-applied voltage relationship of the gas sensor of Example 4 of the first embodiment with that of Comparative example 1 is illustrated. The curves of Groups (III) and (IV) respectively represent results of duplicate experiments in which the detecting current is measured at an applied voltage range of 0 volt to 10 volts using Example 4 and Comparative example 4. The gas sensor of Example 4 has the electric-conduction enhancing layer 42 made of PEDOT, the gas detecting layer 5 made of P3HT, and the second gaps 413 of the second electrode 41 with a width of 10 micrometers (μm).

The gas sensor of Comparative example 4 has a structure and a constituting composition similar to that of the Example 4 except for the omission of the electric-conduction enhancing layer 42.

Figure 11:
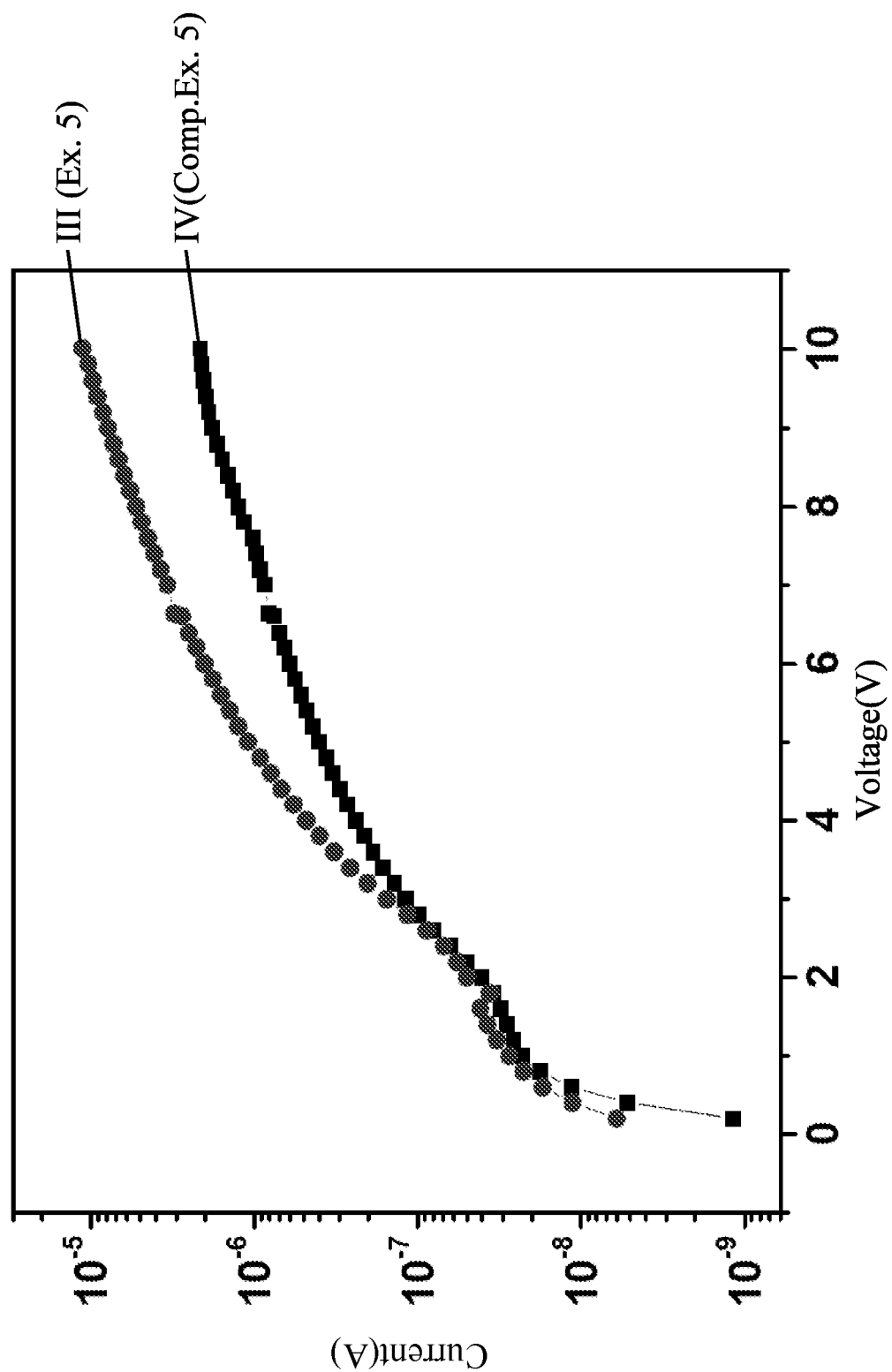
FIG. 11 is a graph of current versus voltage illustrating comparison of a detecting current-applied voltage relationship of Example 5 of the first embodiment with that of Comparative Example 5.
Figure 12:
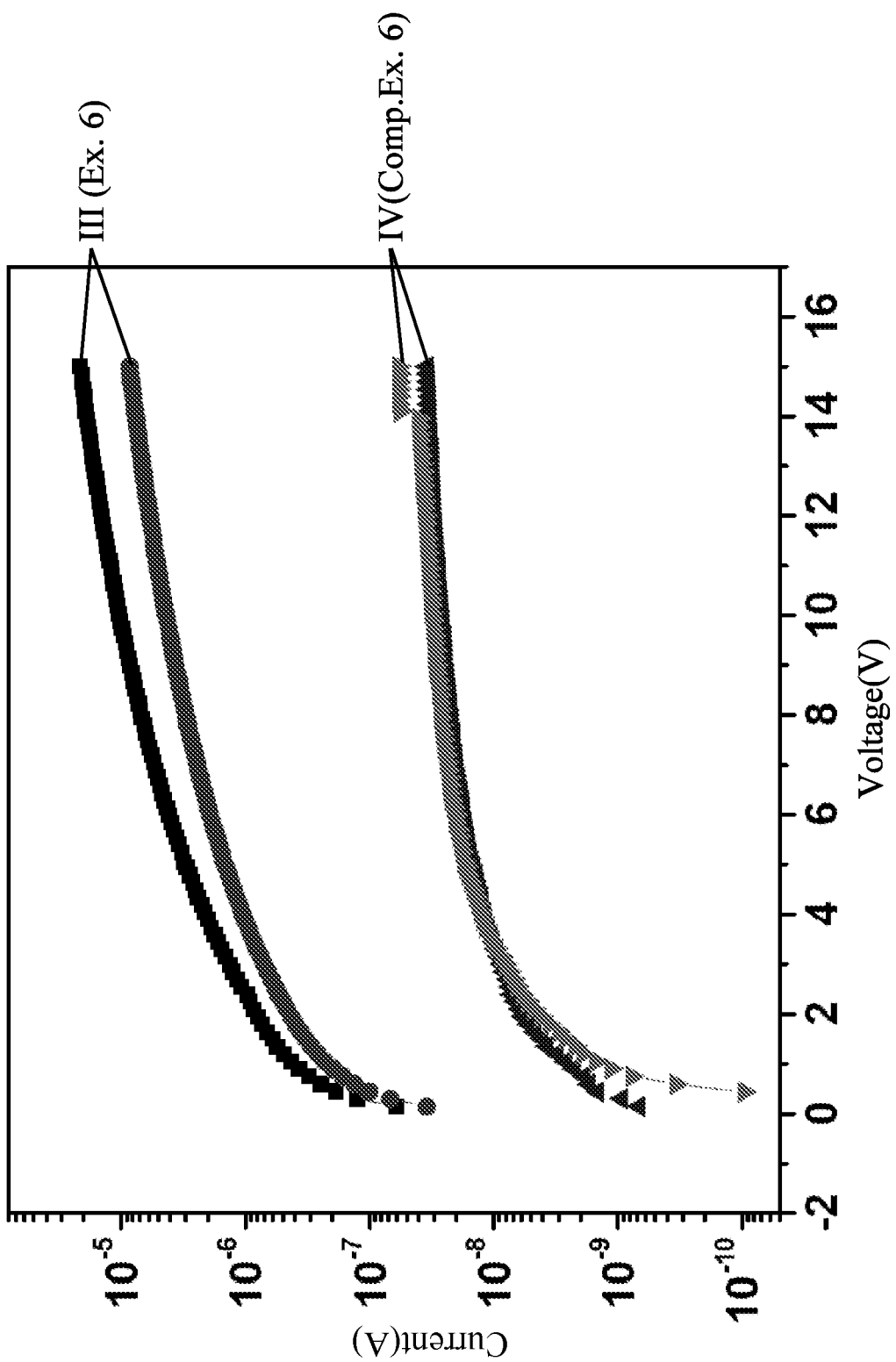
FIG. 12 is a graph of current versus voltage illustrating comparison of a detecting current-applied voltage relationship of Example 6 of the first embodiment with that of Comparative Example 6.
Figure 13:
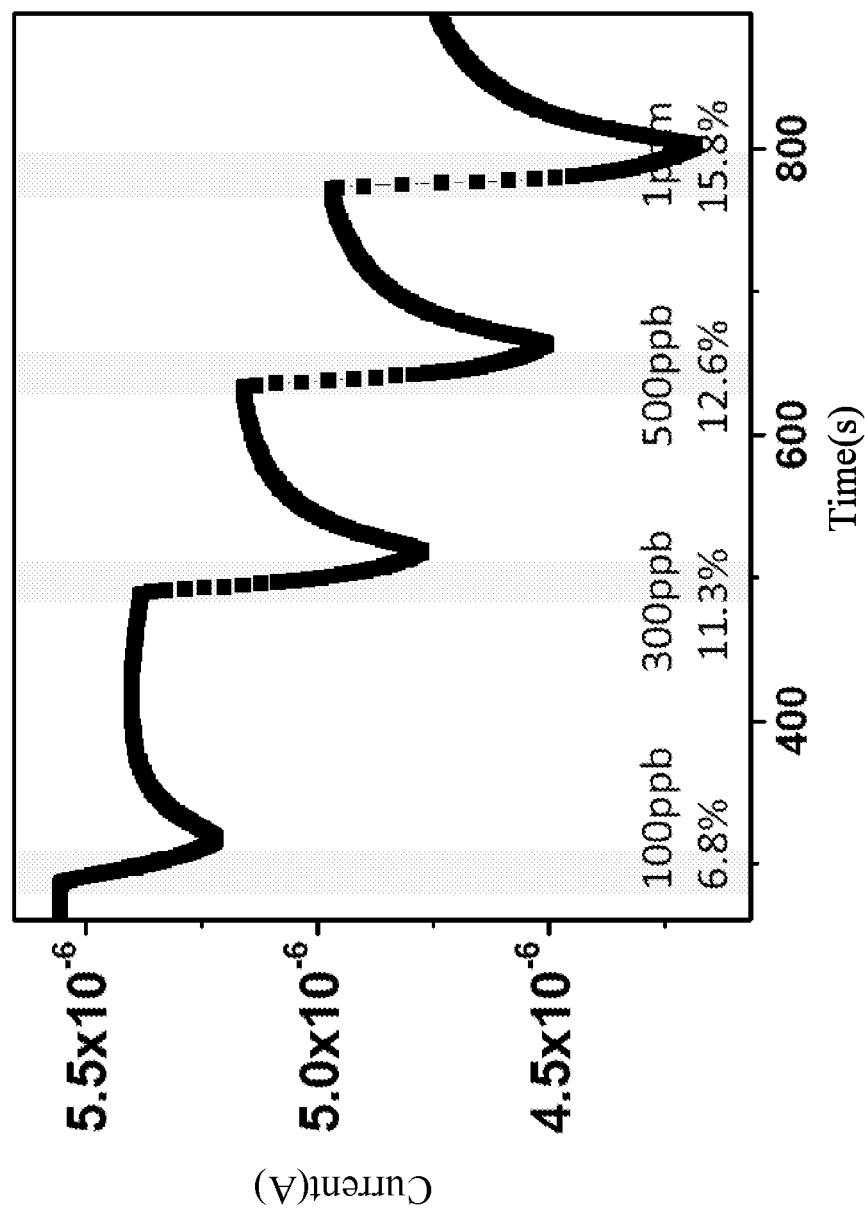
FIG. 13 is a graph of current over time for illustrating ammonia detection using the gas sensor of Example 4 of the first embodiment.
Figure 14:
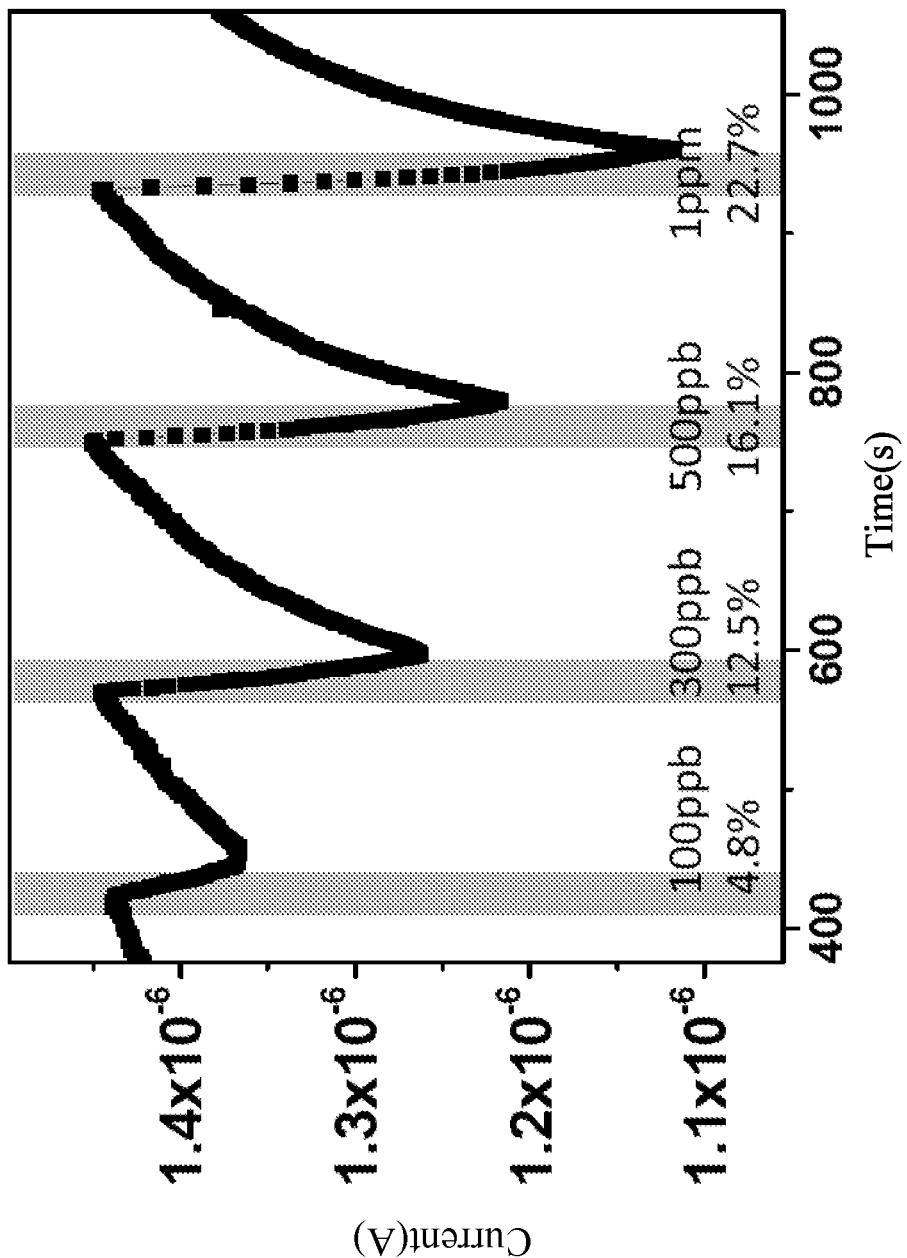
FIG. 14 is a graph of current over time for illustrating ammonia detection using the gas sensor of Comparative Example 4.
Figure 15:
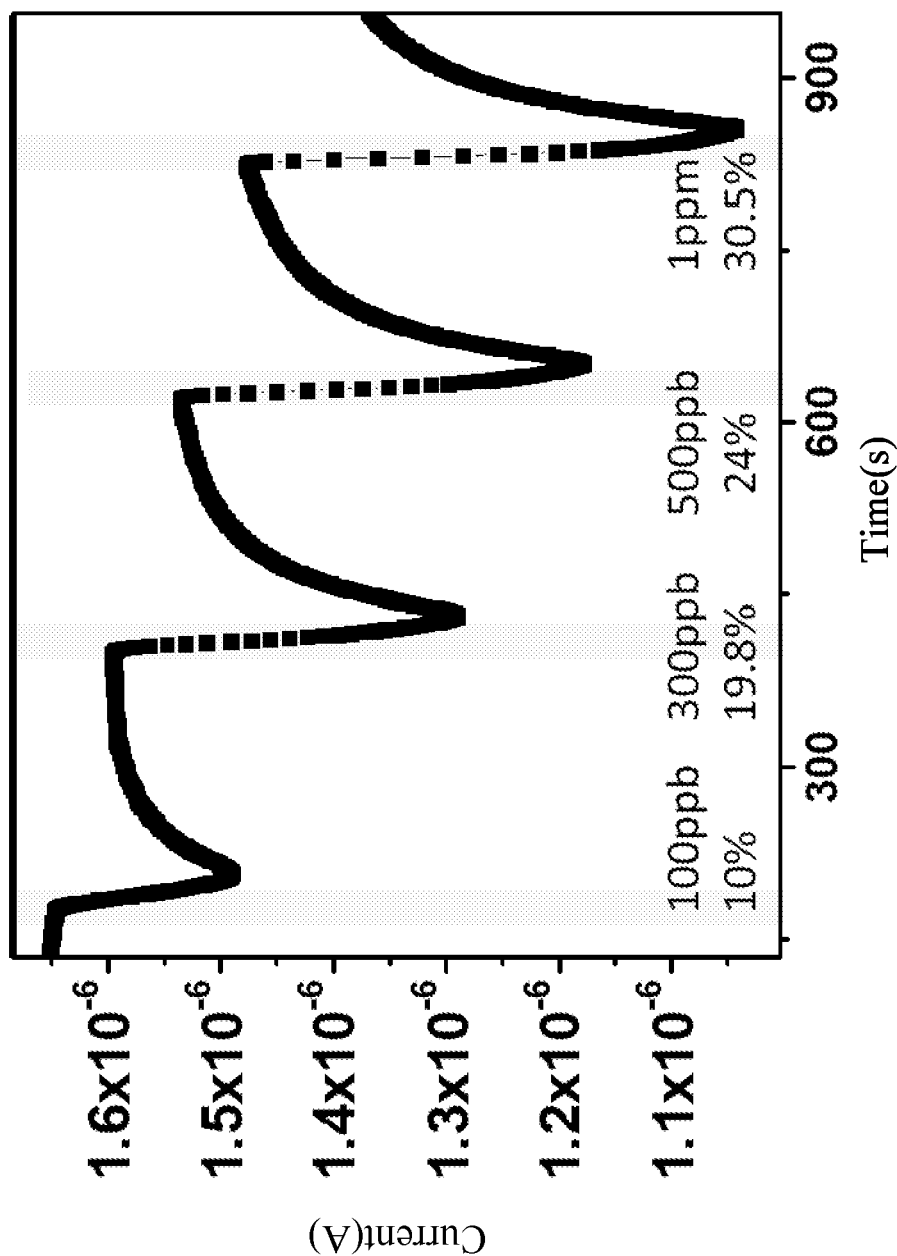
FIG. 15 is a graph of current over time for illustrating ammonia detection using the gas sensor of Example 5 of the first embodiment.
Figure 16:
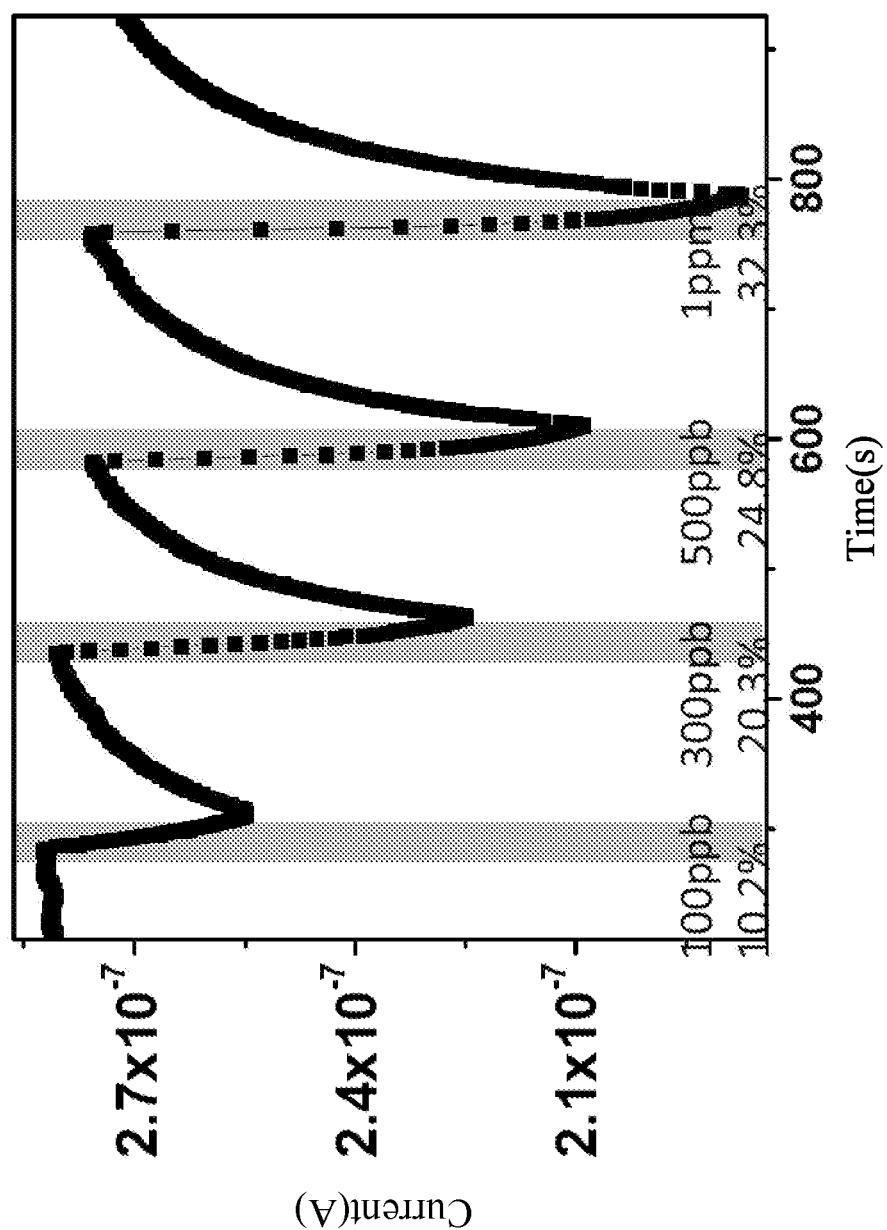
FIG. 16 is a graph of current over time for illustrating ammonia detection using the gas sensor of Comparative Example 5.
Figure 17:
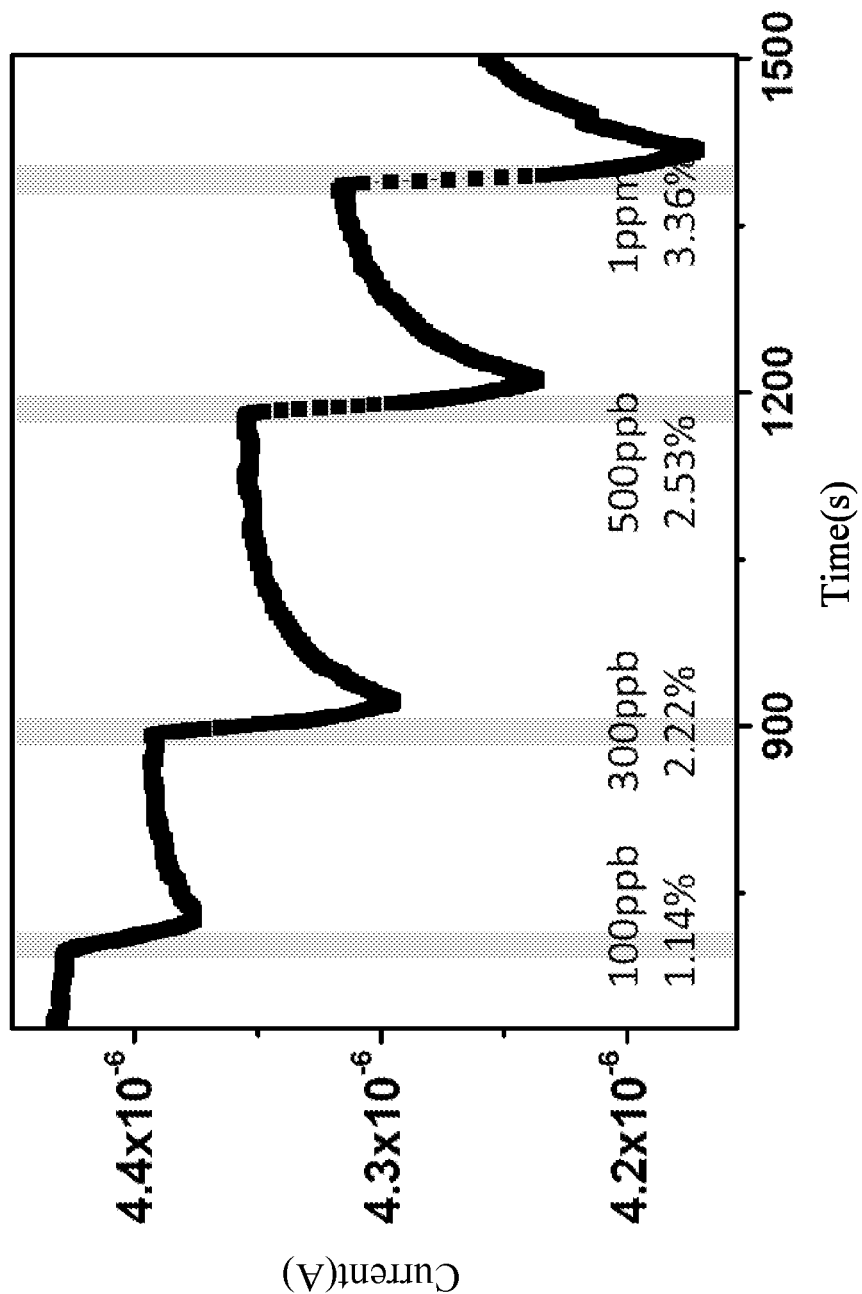
FIG. 17 is a graph of current over time for illustrating ammonia detection using the gas sensor of Example 6 of the first embodiment.
Figure 18:
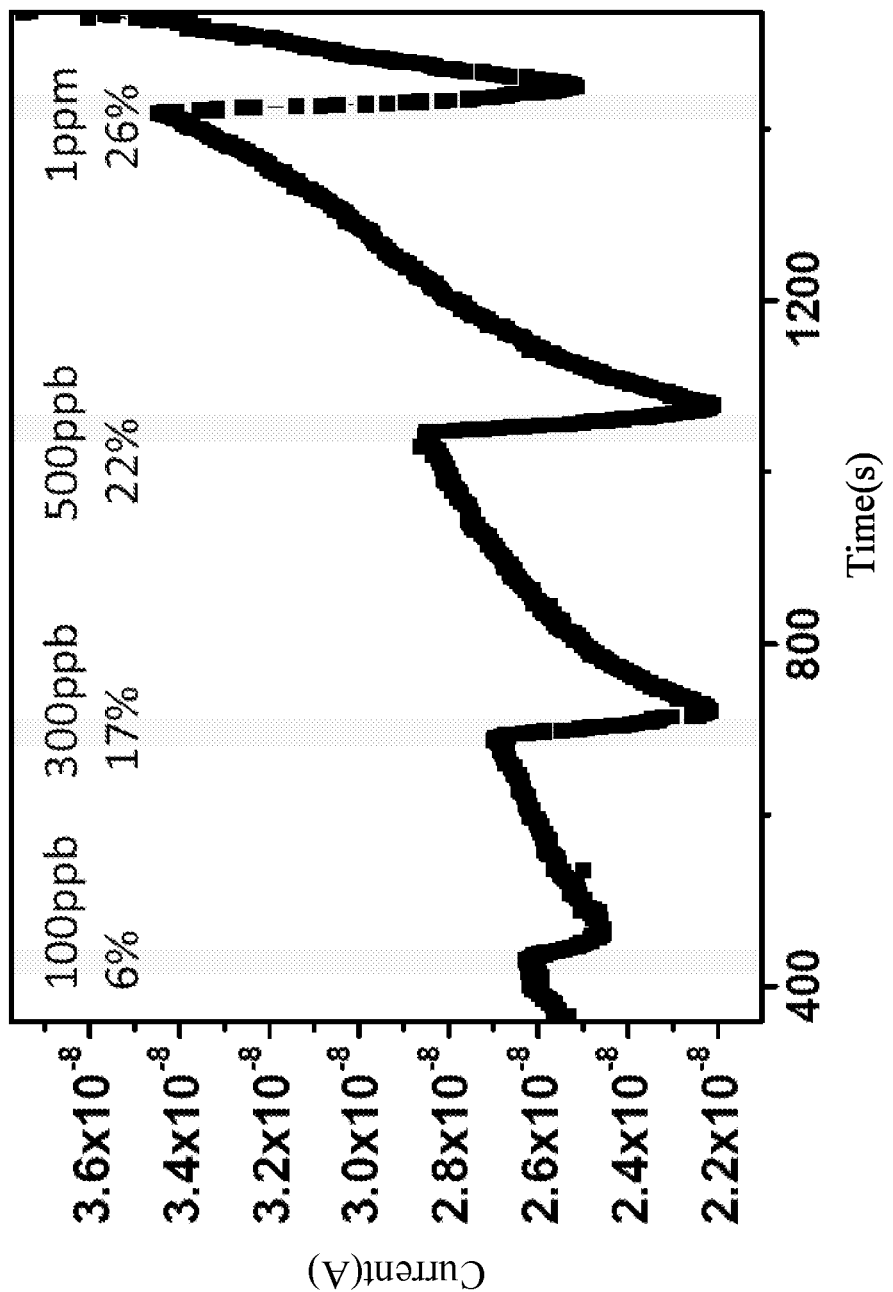
FIG. 18 is a graph of current over time for illustrating ammonia detection using the gas sensor of Comparative Example 6.
Figure 19:
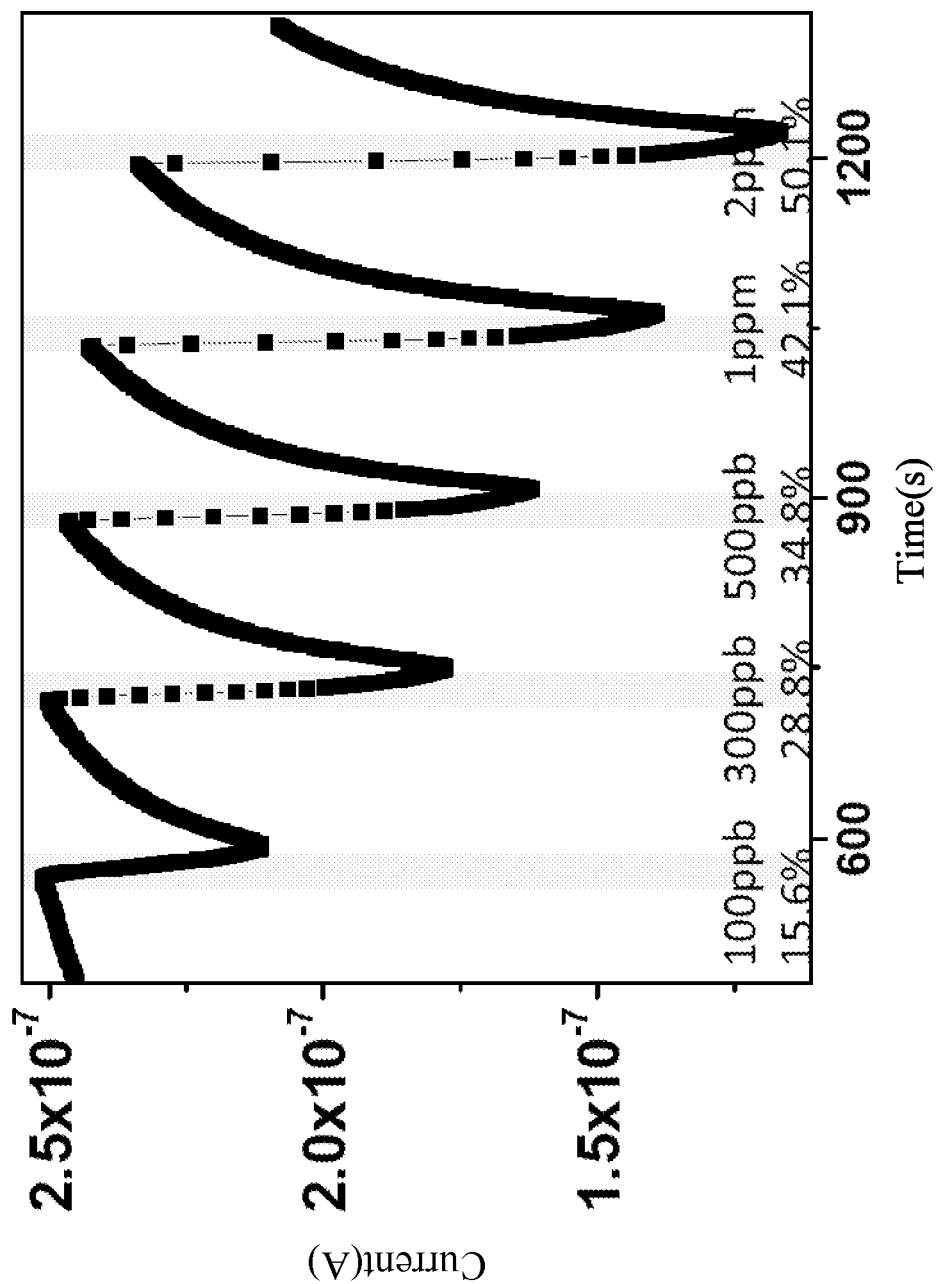
FIG. 19 is a graph of current over time for illustrating ammonia detection using the gas sensor of Example 1 of the first embodiment.
Figure 20:
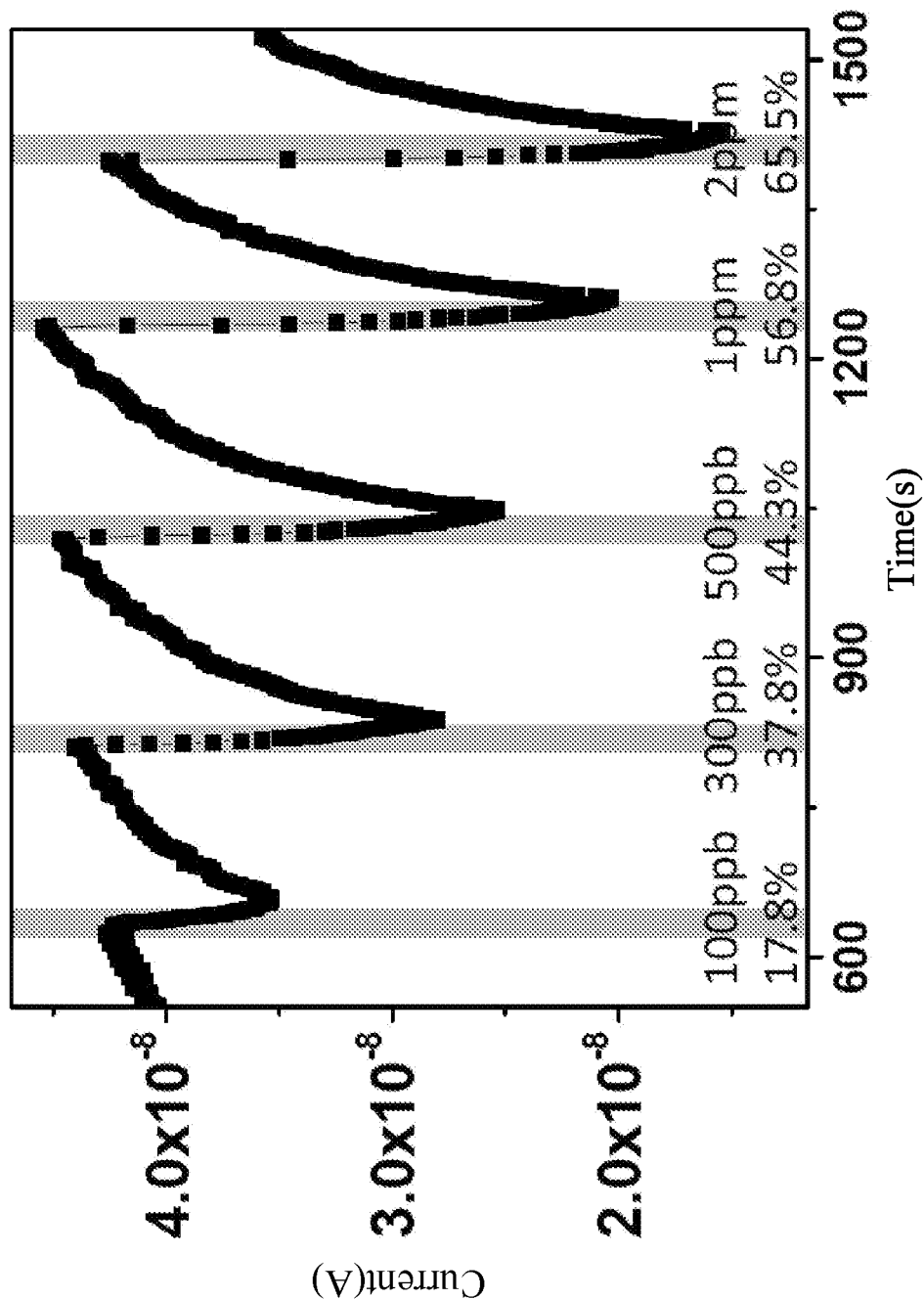
FIG. 20 is a graph of current over time for illustrating ammonia detection using the gas sensor of Comparative Example 1.
Figure 21:
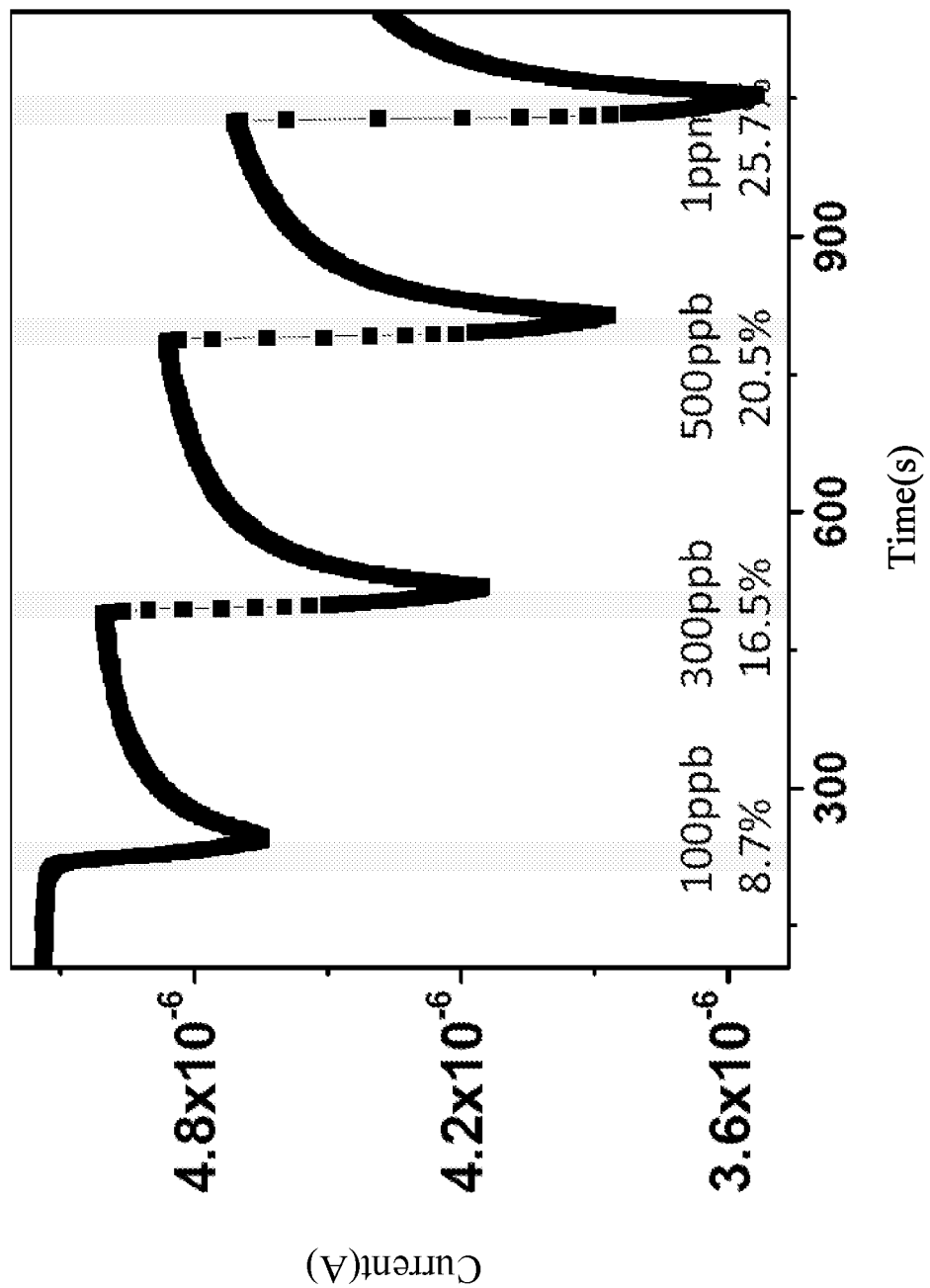
FIG. 21 is a graph of current over time for illustrating ammonia detection using the gas sensor of Example 2 of the first embodiment.
Figure 22:
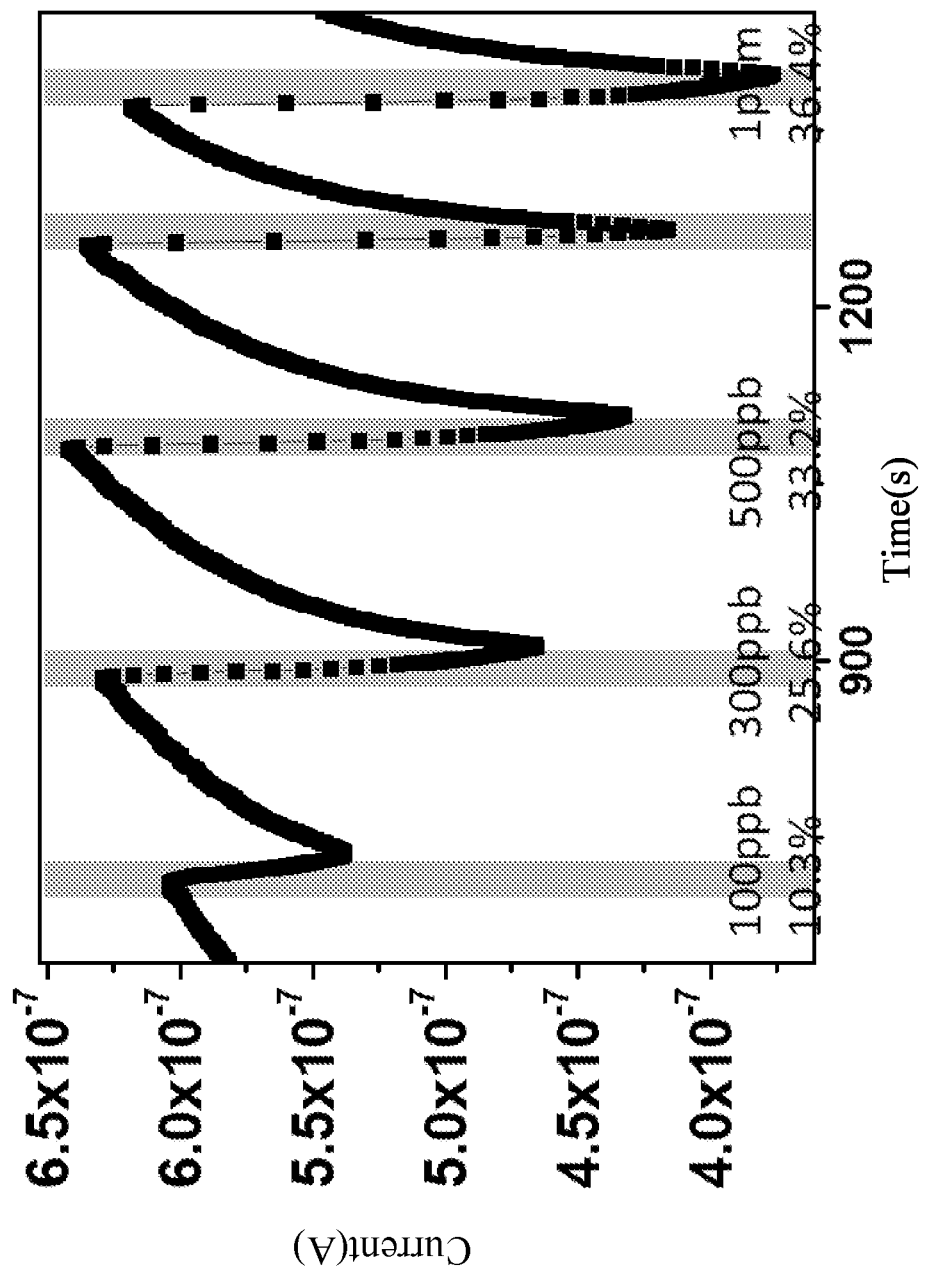
FIG. 22 is a graph of current over time for illustrating ammonia detection using the gas sensor of Comparative Example 2.
Figure 23:
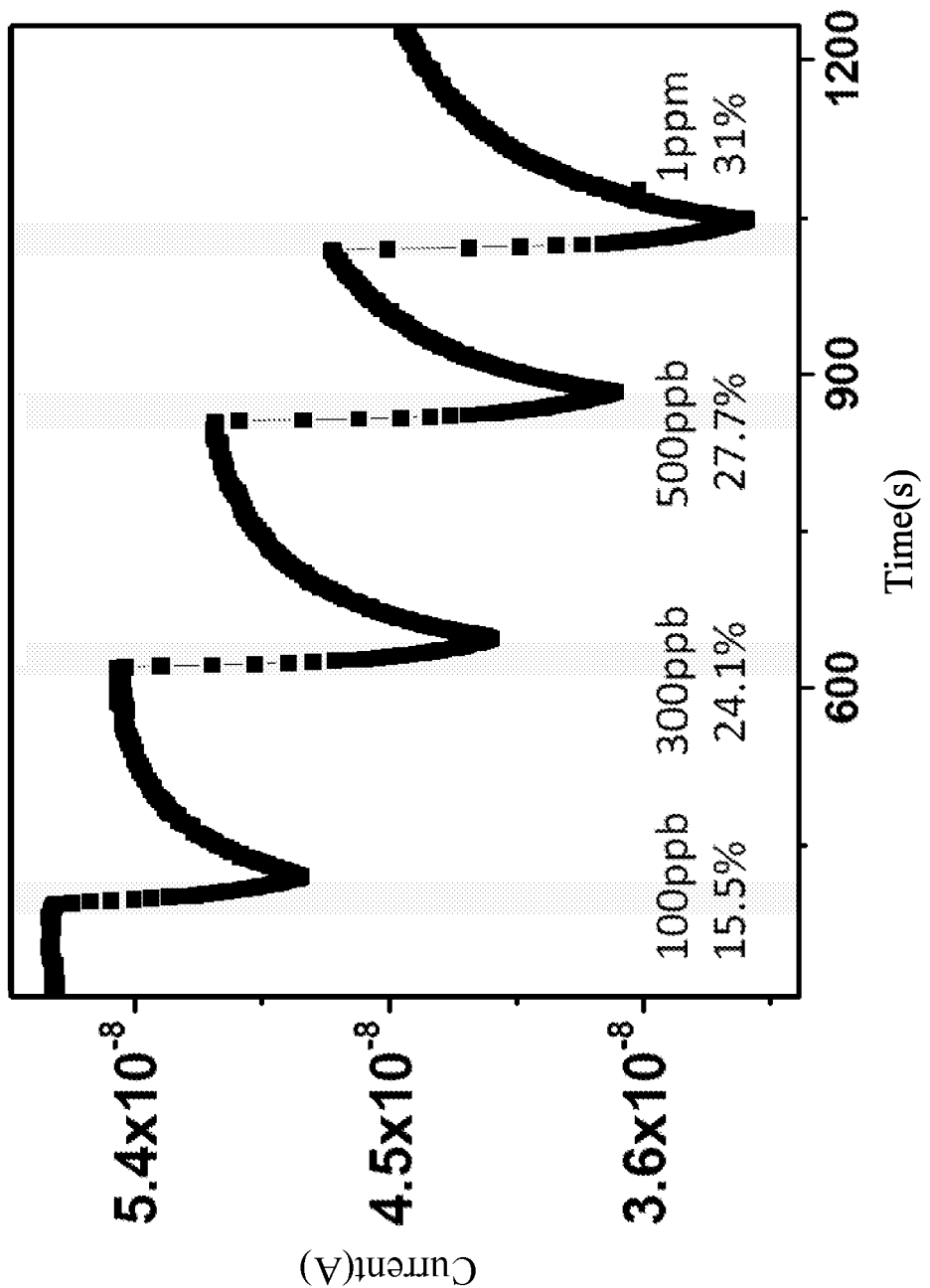
FIG. 23 is a graph of current over time for illustrating ammonia detection using the gas sensor of Example 3 of the first embodiment.
Figure 24:
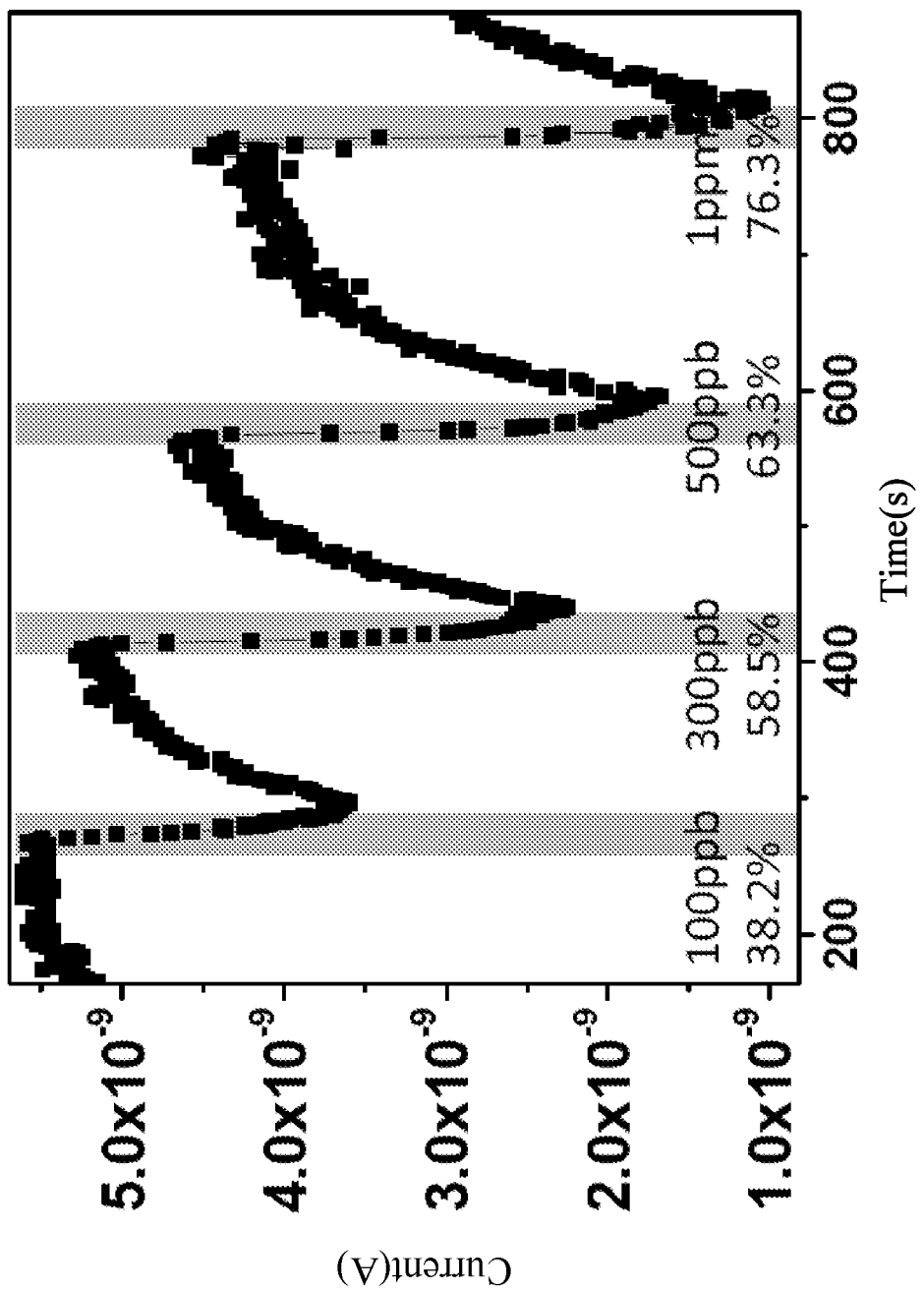
FIG. 24 is a graph of current over time for illustrating ammonia detection using the gas sensor of Comparative Example 3.

FIGS. 11 to 12 respectively illustrate comparison of the detecting current-applied voltage relationship of the gas sensor of Examples 5 and 6 of the first embodiment with that of Comparative examples 5 and 6, in a manner similar to FIG. 10. However, the results shown in FIG. 11 are from a single experiment. The gas sensors of Examples 5 and 6 have a structure and a constituting composition similar to that of Example 4, but the widths of the second gaps 413 of the second electrodes 41 thereof are 20 μm and 80 μm, respectively. Comparative examples 5 and 6 have structures and constituting compositions respectively similar to that of Examples 5 and 6, but both lack the electric-conduction enhancing layer 42.

From the results shown in FIGS. 7 to 12, it can be seen that regardless of the material used for making the gas detecting layer 5, the gas sensors of Examples 1 to 6 correspondingly have a higher detecting current with the same voltage relative to the gas sensors of Comparative Examples 1 to 6 where the electric-conduction enhancing layer 42 is omitted. This shows that the electric-conduction enhancing layer 42 can cooperate with the second electrode 41 to increase the detecting current. Furthermore, it can also be seen from the graphs that variations in the width of the second gaps 413 do not have a large effect on the results of the measurements of the detecting current-applied voltage relationship, thus making the gas sensor of the disclosure suitable for mass production.

Referring to FIGS. 13 to 18, the gas sensors of Examples 4 to 6 and Comparative Examples 4 to 6 are used to perform tests for ammonia detection at different concentrations, the detecting current being measured over time. The applied voltage during the tests is 5 volts for FIGS. 13 and 14, 5 volts for FIGS. 15 and 16, and 10 volts for FIGS. 17 and 18. The gas sensors of Examples 4 to 6 are respectively used in the tests of FIGS. 13, 15, and 17, and the gas sensors of Comparative Examples 4 to 6 are respectively used in the tests of FIGS. 14, 16 and 18.

From the results shown in FIGS. 13 to 18, it can be seen that the electric-conduction enhancing layer 42 of the gas sensor of the disclosure can cooperate with the second electrode 41 to increase the detecting current, such that the gas sensor of the disclosure may produce a larger detecting current even when the applied voltage is low.

Referring to FIGS. 19 to 24, the gas sensors of Examples 1 to 3 and Comparative Examples 1 to 3 are subjected to tests at different ammonia concentrations. The applied voltage applied during the test is 5 volts for FIGS. 19 and 20, 5 volts for FIGS. 21 and 22, and 10 volts for FIGS. 23 and 24. The gas sensors of Examples 1 to 3 are respectively used in the tests of FIGS. 13, 15, and 17, and the gas sensors of Comparative Examples 1 to 3 are respectively used in the tests of FIGS. 14, 16 and 18.

From the results shown in FIGS. 19 to 24, it can be seen that with different widths of the second gaps 413 and at different voltages, the electric-conduction enhancing layer 42 of the gas sensor of the disclosure can still cooperate with the second electrode 41 to increase the detecting current, such that the gas sensor of the disclosure may produce a larger detecting current even when the voltage is low.

In sum, the gas sensor of the disclosure uses the second electrode 41 cooperatively with the electric-conduction enhancing layer 42 to raise the detecting current in order to increase the sensitivity of the detecting of the gas to be detected. Such a configuration is also easier to produce relative to the conventional gas sensor with microspheres, thus making the gas sensor of the disclosure more suitable for mass production.

In the description above, for the purposes of explanation, numerous specific details have been set forth in order to provide a thorough understanding of the embodiments. It will be apparent, however, to one skilled in the art, that one or more other embodiments maybe practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A gas sensor comprising:
   a first electrode;
   a gas detecting layer disposed on said first electrode;
   an electric-conduction enhanced electrode unit being electrically connected to said first electrode and said gas detecting layer and including an electric-conduction enhancing layer and a second electrode electrically connected to said electric-conduction enhancing layer, said electric-conduction enhancing layer being electrically connected to said gas detecting layer and being made of an electrically conductive organic material,
   wherein said second electrode of said electric-conduction enhanced electrode unit includes a plurality of spaced-apart electrode portions formed on said gas detecting layer and interposed between said electric-conduction enhancing layer and said gas detecting layer, any two adjacent ones of said electrode portions being formed with a second gap therebetween to expose said gas detecting layer from said second gap; and wherein said electric-conduction enhancing layer extends into said second gaps to be in contact with said gas detecting layer.

2. The gas sensor as claimed in claim 1, wherein each of said gaps has a width ranging from 1 micrometer to 200 micrometers.

3. The gas sensor as claimed in claim 1, wherein said electrically conductive organic material is selected from the group consisting of poly(3,4-ethylenedioxythiophene), polystyrene sulfonate, polypyrrole, polythiophene, polyphenylene sulfide, polyaniline, polyacetylene, poly(p-phenylene vinylene), and combinations thereof.

4. The gas sensor as claimed in claim 1, wherein:
   said gas detecting layer has a first surface and a second surface opposite to said first surface,
   said first electrode is disposed on said first surface of said gas detecting layer, and
   said electrode portions is disposed on said second surface of said gas detecting layer.

5. The gas sensor as claimed in claim 4, wherein said first electrode is directly disposed on said first surface of said gas detecting layer.

6. The gas sensor as claimed in claim 4, wherein said electrode portions are directly disposed on said second surface of said gas detecting layer.

7. The gas sensor as claimed in claim 1, wherein said gas detecting layer is in full and direct contact with said first electrode.

8. The gas sensor as claimed in claim 1, wherein said gas detecting layer is composed of an absorbent base material with supporting properties and a gas detecting material absorbed onto the absorbent base material.

9. The gas sensor as claimed in claim 8, wherein said absorbent base material is porous.

10. The gas sensor as claimed in claim 8, wherein said absorbent base material is selected from the group consisting of oil blotting paper and tissue paper.

11. The gas sensor as claimed in claim 1, wherein said first electrode is made of an electrically conductive material selected from the group consisting of a metal, an electrically conductive metallic compound and an electrically conductive organic material.

12. The gas sensor as claimed in claim 1, wherein said second electrode is made of an electrically conductive material selected from the group consisting of a metal, a metallic compound and an organic material.

13. The gas sensor as claimed in claim 1, wherein said electric-conduction enhancing layer extending into said gaps is in direct contact with said gas detecting layer.

* * * * *

UNITED STATES PATENT AND TRADEMARK OFFICE
CERTIFICATE OF CORRECTION

PATENT NO. : 12,253,489 B2
APPLICATION NO. : 17/975977
DATED : March 18, 2025
INVENTOR(S) : Hsiao-Wen Zan et al.

Page 1 of 1

It is certified that error appears in the above-identified patent and that said Letters Patent is hereby corrected as shown below:

In the Claims

Column 10, Claim 1, Line 18, "a second gap" should read --a gap--.
Column 10, Claim 1, Line 19, "said second gap" should read --said gap--.
Column 10, Claim 1, Line 21, "second gaps" should read --gaps--.

Signed and Sealed this
Eighth Day of July, 2025

Coke Morgan Stewart
*Acting Director of the United States Patent and Trademark Office*